ND

United States Patent
Yamashita et al.

(12) United States Patent
(10) Patent No.: US 11,533,971 B2
(45) Date of Patent: Dec. 27, 2022

(54) MOLDED SURFACE FASTENER

(71) Applicant: YKK Corporation, Tokyo (JP)

(72) Inventors: Hiroyuki Yamashita, Kurobe (JP);
Yoshiyuki Fukuhara, Kurobe (JP);
Ryosuke Tanimoto, Kurobe (JP);
Makoto Takekawa, Kurobe (JP);
Shoichi Yokoyama, Kurobe (JP)

(73) Assignee: YKK Corporation, Tokyo (JP)

( * ) Notice: Subject to any disclaimer, the term of this patent is extended or adjusted under 35 U.S.C. 154(b) by 0 days.

(21) Appl. No.: 17/257,883

(22) PCT Filed: Jul. 9, 2018

(86) PCT No.: PCT/JP2018/025907
§ 371 (c)(1),
(2) Date: Jan. 5, 2021

(87) PCT Pub. No.: WO2020/012537
PCT Pub. Date: Jan. 16, 2020

(65) Prior Publication Data
US 2021/0267320 A1 Sep. 2, 2021

(51) Int. Cl.
A44B 18/00 (2006.01)
(52) U.S. Cl.
CPC ...... A44B 18/0049 (2013.01); A44B 18/0065 (2013.01); Y10T 24/27 (2015.01)
(58) Field of Classification Search
CPC .. A44B 18/0049; A44B 18/0065; Y10T 24/27
See application file for complete search history.

(56) References Cited

U.S. PATENT DOCUMENTS 5,067,210 A    11/1991 Kayaki
6,209,177 B1    4/2001 Murasaki
(Continued)

FOREIGN PATENT DOCUMENTS

CN    1307455 A    8/2001
CN    1617682 A    5/2005
(Continued)

OTHER PUBLICATIONS

International Search Report, PCT Application No. PCT/JP2018/025907, dated Sep. 4, 2018.
(Continued)

Primary Examiner — Robert Sandy
Assistant Examiner — Michael S Lee
(74) Attorney, Agent, or Firm — Kilpatrick Townsend & Stockton LLP

(57) ABSTRACT

In a molded surface fastener in which an engaging element includes at least two engaging pawl portions protruded outward, a plurality of the engaging elements is disposed in a line along a machine direction to form an element row, a plurality of the element rows is arranged side by side in a cross direction, each of the engaging elements has, as the engaging pawl portions, at least a pair of symmetrical engaging pawl portions which are disposed each other at symmetrical positions in the cross direction and are respectively protruded in the cross direction sides, and a plurality of the engaging elements is arranged in a staggered pattern. Thereby, the molded surface fastener can appropriately and stably exert desired performance such as peel strength with respect to more types of non-woven fabrics.

10 Claims, 14 Drawing Sheets

(56) References Cited

U.S. PATENT DOCUMENTS

| | | |
|---|---|---|
| 6,627,133 B1 | 9/2003 | Tuma |
| 11,291,275 B2* | 4/2022 | Fukuhara ................ B29C 43/26 |
| 2003/0131453 A1 | 7/2003 | Clarner et al. |
| 2005/0081344 A1* | 4/2005 | Clarner .............. A44B 18/0061 24/452 |
| 2009/0126165 A1 | 5/2009 | West |
| 2013/0067702 A1 | 3/2013 | Tuma |
| 2014/0237779 A1 | 8/2014 | Gallant et al. |
| 2015/0275941 A1 | 10/2015 | Nisogi |
| 2016/0366991 A1* | 12/2016 | Mascarenhas ...... B29C 44/1233 |
| 2017/0295890 A1 | 10/2017 | Imai et al. |
| 2018/0360170 A1 | 12/2018 | Fukuhara et al. |
| 2018/0368534 A1 | 12/2018 | Fukuhara et al. |
| 2019/0008239 A1 | 1/2019 | Fukuhara et al. |
| 2019/0016023 A1* | 1/2019 | Parellada Armela ... B29C 43/46 |
| 2020/0196715 A1 | 6/2020 | Fukuhara et al. |
| 2020/0196716 A1 | 6/2020 | Fukuhara et al. |
| 2020/0305558 A1* | 10/2020 | Takekawa .......... A44B 18/0049 |
| 2021/0106101 A1 | 4/2021 | Fukuhara et al. |
| 2021/0393001 A1 | 12/2021 | Fukuhara et al. |

FOREIGN PATENT DOCUMENTS

| | | |
|---|---|---|
| CN | 102984965 A | 3/2013 |
| CN | 104812262 A | 7/2015 |
| CN | 108430251 A | 8/2018 |
| JP | H03-55176 A | 5/1991 |
| JP | H11-206422 A | 8/1999 |
| JP | 2013-123438 A | 6/2013 |
| JP | 2014-076210 A | 5/2014 |
| JP | 2017-189353 A | 10/2017 |
| TW | 201722304 A | 7/2017 |
| WO | 2017/109902 A1 | 6/2017 |
| WO | 2017/110106 A1 | 6/2017 |
| WO | 2017187103 A1 | 11/2017 |

OTHER PUBLICATIONS

Extended European Search Report, European Patent Application No. 18925990.6, dated Jun. 23, 2021, 8 pages.

Office Action, Taiwanese Patent Application No. 107137708, dated Mar. 28, 2019, 11 pages.

Decision of Refusal, Taiwanese Patent Application No. 107137708, dated Jul. 22, 2019, 8 pages.

Office Action, Chinese Patent Application No. 201880095468.X, dated Jun. 15, 2022, 16 pages.

\* cited by examiner

MOLDED SURFACE FASTENER

TECHNICAL FIELD

The present invention relates to a molded surface fastener having a flat plate-shaped base portion and a plurality of engaging elements standing on an upper surface of the base portion.

BACKGROUND ART

Conventionally, surface fastener products in which a female surface fastener having a plurality of loops and a male molded surface fastener which is attachable and detachable with respect to the female surface fastener are used in combination as a pair are known. The male molded surface fastener manufactured by molding synthetic resin, for example, is formed such that a plurality of male engaging elements having a mushroom shape or the like stand on an upper surface of a flat plate-shaped base portion.

The surface fastener products having such a male surface fastener are now broadly used in a wide variety of goods, for example, often used for goods wearable to human bodies such as disposable diapers, infant diaper covers, supporters for protecting joints in limbs, waist corset (lumbago belt), and gloves.

In a molded surface fastener used for disposable diapers or the like, a J shape, a palm tree shape, a mushroom shape and the like are generally known as typical shapes of male engaging elements. For example, the J-shaped engaging element are protruded upward from a base portion and has a shape in which an upper end part is curved like a hook.

A palm tree-shaped engaging element has a shape including a stem portion which is protruded vertically from a base portion and a hook-shaped engaging head portion extending in a curved manner in two directions opposite to each other from an upper end of the stem portion. A mushroom-shaped engaging element has a shape including a stem portion which is protruded vertically from a base portion and a disk-shaped engaging head portion integrally formed to be disposed above the stem portion and to bulge outward from an entire upper end outer periphery of the stem portion in a plan view of the engaging element.

International Publication No. 2017/109902 (Patent Document 1) discloses, as one of shapes of the engaging element, an engaging element 90 having a substantially truncated cone-shaped stem portion 91 standing on a base portion 81, an engaging head portion 92 formed integrally on the stem portion 91, and a plurality of engaging pawl portions (pawl portion) 93 which is protruded outward from an outer peripheral edge part of the engaging head portion 92, as shown in FIG. 21 and FIG. 22.

In a case of a molded surface fastener 80 as shown in FIG. 21 and FIG. 22, two engaging pawl portions 93 are formed to be protruded in directions opposite to each other in a cross direction (CD) perpendicular to a machine direction from a middle part of the engaging head portion 92 in a machine direction (MD) in a plan view of the engaging element 90, and to be sloped or curved downward from the outer peripheral edge part of the engaging head portion 92 toward the base portion 81.

Further, the international publication No. 2017/110106 (Patent Document 2), for example, discloses an engaging element having a substantially truncated cone-shaped stem portion standing on a base portion, a rib portion provided projectingly on an upper surface of the stem portion, and engaging pawl portions (micro pawl portions) which are protruded downward from end edge parts of the rib portion toward the base portion. The Patent Document 2 also discloses, as another embodiment, an engaging element having a substantially truncated cone-shaped stem portion standing on a base portion and engaging pawl portions (micro pawl portions) which are protruded downward from an outer peripheral side surface of the stem portion.

In the above-mentioned Patent Document 1 and Patent Document 2, a plurality of the engaging elements is, as shown in FIG. 21, for example, arranged to be aligned regularly along the machine direction (MD) and the cross direction (CD) of the molded surface fastener. Thus, the molded surface fastener has a plurality of MD element rows formed by disposing the plurality of the engaging elements along the machine direction and a plurality of CD element rows formed by disposing the plurality of the engaging elements along the cross direction.

PRIOR ART DOCUMENTS

Patent Documents

Patent Document 1: WO 2017/109902
Patent Document 2: WO 2017/110106

SUMMARY OF INVENTION

Problems to be Solved by the Invention

In the molded surface fastener 80 described in Patent Document 1 and the molded surface fastener described in Patent Document 2, a plurality of the engaging elements is arranged to be aligned regularly along the machine direction (MD) and the cross direction (CD) as mentioned above. However, as shown in FIG. 21, for example, when the two engaging pawl portions (pawl portions) 93 of the engaging element 90 are protruded toward opposite directions to each other from a middle part of the engaging head portion 92 in the machine direction, between the MD element rows that are adjacent to each other in the cross direction (CD), the engaging element 90 having a short separation distance between the engaging pawl portions 93 and the engaging element 90 having a long separation distance between the engaging pawl portions 93 are respectively arranged with respect to one engaging element 90.

Specifically, when one engaging element 90a disposed in the MD element row is used as a reference, for example, the MD element row adjacent to the element row in the cross direction has one engaging element 90 (first engaging element 90b) which is disposed at a position closest to the reference engaging element 90a and two engaging elements 90 (second engaging element 90c) which are disposed adjacent to the first engaging element 90b in the machine direction and to be the second closest to the reference engaging element 90a. In this case, when the distance between the engaging pawl portion 93 of the reference engaging element 90a and the engaging pawl portion 93 of the first engaging element 90b is determined as a first separation distance D2, and the distance between the engaging pawl portion 93 of the reference engaging element 90a and the engaging pawl portion 93 of the second engaging element 90c is determined as the second separation distance D3, the first separation distance D2 is inevitably shorter than the second separation distance D3.

However, when the first separation distance D2 and the second separation distance D3 having different sizes to each other for each engaging element 90 are provided between the MD element rows adjacent to each other in the cross direction as above, the performance of the molded surface fastener 80 has been sometimes affected by the structure of the non-woven fabric (female surface fastener) to be engaged with the male molded surface fastener 80.

In a case of a non-woven fabric or the like having relatively thick loops, for example, the loops of the non-woven fabric are less likely to enter between the engaging elements 90 of the first separation distance D2 having a small separation distance between the engaging pawl portions 93. As a result, the loops are less likely to be engaged with the engaging elements 90, and thus the engaging strength (peel strength) is sometimes lowered. Further, depending on the structure of the non-woven fabric, although the loops of the non-woven fabric are smoothly inserted between the engaging elements 90 of the first separation distance D2, the loops are entered excessively between the engaging elements 90 of the second separation distance D3 having a large separation distance between the engaging pawl portions 93. Thereby, a part of the entered loops may be rather less likely to be caught in the engaging elements 90.

Therefore, in the molded surface fastener 80 provided with two types of the separation distances D2 and D3 as described above, good and bad compatibility with the non-woven fabric (strengths and weaknesses of the non-woven fabric) is likely to occur. Thus, when the molded surface fastener is used for products such as disposable diapers, for example, it sometimes has been necessary to consider the two types of the separation distances between the engaging pawl portions for each engaging element, and to select a non-woven fabric which is capable of engaging properly with the male molded surface fastener. As a result, there was a possibility of the limited use of the molded surface fastener and the increased cost of the final products.

The present invention has been made in view of the above-described conventional problems, and an object is to provide a molded surface fastener in which the engaging pawl portions of the engaging element are disposed at symmetrical positions with each other with respect to a center line along the machine direction, a difference in easiness of entering loops between the engaging elements in the element rows adjacent to the cross direction can be less likely to occur, and performance such as peel strength can be appropriately and stably exerted for more types of nonwoven fabrics.

Means for Solving the Problems

In order to achieve the above object, a molded surface fastener provided by the present invention is, as the most main characteristics, a molded surface fastener made of synthetic resin having a flat plate-shaped base portion formed to be long in a machine direction and a plurality of engaging elements standing on an upper surface of the base portion, in which the engaging element includes a stem portion standing on the upper surface of the base portion and at least two engaging pawl portions protruding outward at a top end part of the engaging element, wherein the plurality of the engaging elements is disposed in a line at a predetermined pitch interval along the machine direction of the base portion to form an element row, a plurality of the element rows is arranged side by side in a cross direction perpendicular to the machine direction, each of the engaging elements has, as the engaging pawl portions, at least a pair of symmetrical engaging pawl portions which are disposed at symmetrical positions with each other with respect to an imaginary center line located in a middle of the cross direction of the stem portion in a plan view of the engaging element, and are protruded respectively in the cross direction sides, and the engaging elements in each element row are disposed at a position shifted by half the size of the pitch interval in the machine direction with respect to a position of the engaging elements in the element rows adjacent to each other in the cross direction.

In the molded surface fastener according to the present invention, it is preferable that a plurality of the element rows is disposed at a predetermined pitch interval in the cross direction, widthwise space regions in which the engaging elements are not provided are disposed along the machine direction between the element rows adjacent to each other in the cross direction, and the pitch interval of the element rows in the cross direction is larger than half the size of the pitch interval in the machine direction.

Further, it is preferable that, in a plan view of the molded surface fastener, a minimum element separation distance between the engaging elements adjacent to each other in the machine direction in each element row is larger than a maximum value of a dimension in the machine direction of the engaging element in other element rows adjacent to the element row in the cross direction, and lengthwise space regions in which the engaging elements are not provided are disposed along the cross direction over the entire molded surface fastener in the cross direction.

In this case, it is preferable that widthwise space regions in which the engaging elements are not provided are disposed along the machine direction between the element rows adjacent to each other in the cross direction, and a dimension of the lengthwise space region in the machine direction is smaller than a dimension of the widthwise space region in the cross direction.

In the molded surface fastener of the present invention, it is possible that, in a plan view of the molded surface fastener, a minimum element separation distance between the engaging elements adjacent to each other in the machine direction in each element row is equal to or smaller than a maximum value of a dimension in the machine direction of the engaging element in other element rows adjacent to the element row in the cross direction.

In the molded surface fastener of the present invention, it is preferable that the engaging elements are formed such that an upper end surface or an upper end cross-section at an upper end part of each stem portion perpendicular to a standing direction of the stem portion has the same shape and same area each other for each element row, and at least two types of the element rows in which the areas of the upper end surfaces or the upper end cross-sections of the stem portions are different from each other are provided.

It is preferable that, as the element rows, first element rows in which the area of an upper end surface or an upper end cross-section at an upper end part in each of the stem portions perpendicular to a standing direction of the stem portion is a first size and second element rows in which the area of the upper end surface or the upper end cross-section in each of the stem portions is a second size to be larger than the first size are provided, and the first element rows and the second element rows are alternately arranged in the cross direction.

In this case, it is preferable that the upper end surface or the upper end cross-section in each of the stem portions in the first element rows and the upper end surface or the upper end cross-section in each of the stem portions in the second element rows have a shape similar to each other, and a height dimension of each engaging element in the first element rows from the base portion and a height dimension of each engaging element in the second element rows from the base portion are the same.

Further in the molded surface fastener of the present invention, it is preferable that a pair of the symmetrical engaging pawl portions are, in a plan view of the engaging element, disposed in a middle part of the stem portion in the machine direction and protruded each other in opposite directions along the cross direction, and with respect to the engaging elements in each element row, each of the other element rows adjacent to the element row in the cross direction includes two engaging elements in which respective separation distances between the symmetrical engaging pawl portion of the element row and the symmetrical engaging pawl portion of the other element row are equal.

In the molded surface fastener of the present invention, the engaging pawl portions are formed to be sloped or curved downward toward the base portion.

Effects of the Invention

In the molded surface fastener according to the present invention, each of the hook-shaped engaging elements has the stem portion standing on the upper surface of the base portion and at least a pair of symmetrical engaging pawl portions which are disposed at the top end part (upper end part) of the engaging element and protruded outward at the symmetrical positions with each other with respect to the center line located in the middle of the engaging element in the cross direction. In this case, the pair of symmetrical engaging pawl portions are respectively protruded along the cross direction from a part of the engaging element such as the stem portion. The plurality of the engaging elements is disposed in a line at a predetermined (constant) pitch interval along the machine direction of the base portion, thus to form the element rows in the machine direction. Further, a plurality of the element rows in the machine direction is arranged at the same interval in the cross direction.

Further in the present invention, the engaging elements in each element row are disposed at a position shifted by half the size of the pitch interval in the machine direction as mentioned above with respect to a position of the engaging elements in other element rows adjacent to each other of the element row in the cross direction. That is, the engaging elements forming the plurality of element rows are integrally provided on the base portion in a staggered arrangement in which the engaging elements are located alternately between the adjacent element rows in the cross direction. In this case, the protruding direction of the pair of symmetrical engaging pawl portions symmetrically disposed in the cross direction and the direction of shifting the positions of the engaging elements between adjacent element rows are perpendicular to each other.

Since the plurality of the engaging elements has the pair of symmetrical engaging pawl portions respectively protruded in the cross direction sides and are arranged in a staggered pattern as mentioned above, it is possible to less likely to occur a difference in the separation distances of the engaging pawl portions between the engaging elements in the adjacent element rows in the cross direction (in other word, it is possible to make the separation distances of the engaging pawl portions substantially the same size in the plurality of the engaging elements).

That is, in the molded surface fastener of the present invention in which the above-mentioned pair of the symmetrical engaging pawl portions are provided in each engaging element, emphasis is placed on the separation distance (size of the space) between the engaging pawl portions of the two engaging elements between the adjacent element rows in the cross direction, and a staggered pattern is adopted as an arrangement pattern of the engaging elements so that the separation distance between the engaging pawl portions is the same size for more engaging elements.

Therefore, in the molded surface fastener of the present invention, when the loops of the loop member (non-woven fabric, etc.) enter between the engaging elements of the adjacent element rows in the cross direction, it is possible to effectively prevent a difference in the ease of entering the loops due to a difference in the separation distances of the engaging pawl portions. Therefore, the loops can be inserted in the same manner between the engaging pawl portions of any of the engaging elements crossing in the two element rows, thereby a plurality of the loops can be stably engaged with the engaging elements.

As a result, it is possible to make the molded surface fastener less likely to cause strengths and weaknesses for the non-woven fabric, and thus to make the performance such as peel strength (engaging strength) of the molded surface fastener less likely to be affected by the type of the non-woven fabric. That is, the molded surface fastener of the present invention can appropriately and stably exert desired peel strength and the like with respect to more types of non-woven fabrics. Further, thereby, it is possible to prevent that the use of the molded surface fastener is limited due to the compatibility with the non-woven fabric, and to reduce the cost burden on the final products.

In such a molded surface fastener of the present invention, the plurality of the element rows is disposed at a predetermined pitch interval in the cross direction. Between the element rows adjacent to each other in the cross direction, widthwise space regions in the cross direction in which the engaging elements are not provided are continuously provided along the machine direction. Further, in this case, the pitch interval of the element rows in the cross direction is set to be larger than half the size of the pitch interval of the engaging elements in the machine direction.

By increasing the pitch interval of the element rows in the cross direction as described above, it is possible to form the widthwise space regions to be wide in the cross direction, and thereby, to insert and engage more loops between the engaging elements in the adjacent element rows in the cross direction. Further, by forming the widthwise space regions to be wide in the cross direction, when the molded surface fastener of the present invention is cut along the machine direction to form as a narrow shape, for example, the molded surface fastener can be cut in the widthwise space regions. Therefore, it is possible to prevent that cutting processing of the molded surface fastener is hindered by the engaging elements, and to easily cut the molded surface fastener so as to have a predetermined width dimension (dimension in the cross direction).

In the present invention, in a plan view of the molded surface fastener, the minimum element separation distance between the engaging elements adjacent to each other in the machine direction in each element row is set to be larger than the maximum value of the dimension in the machine direction of the engaging element in other element rows adjacent to the element row in the cross direction. Thereby, the lengthwise space regions in the machine direction in which the engaging elements are not provided can be continuously provided along the cross direction over the entire molded surface fastener in the cross direction. Thus, for example, when the molded surface fastener of the present invention is cut along the cross direction, the molded surface fastener can be easily cut over the entire cross direction in the lengthwise space regions.

Further, in this case, between the element rows adjacent to each other in the cross direction, the widthwise space regions in which the engaging elements are not provided are provided continuously along the machine direction, and the dimension of the lengthwise space region in the machine direction is set to be smaller than the dimension of the widthwise space region in the cross direction. Therefore, it is possible to prevent the above-mentioned separation distances between the engaging pawl portions from becoming too large between the adjacent element rows in the cross direction, and thus to stably obtain appropriate peel strength, shear strength, etc. of the molded surface fastener.

Furthermore, in the plan view of the molded surface fastener of the present invention, the minimum element separation distance between the engaging elements adjacent to each other in the machine direction in each element row may be equal to or smaller than a maximum value of the dimension in the machine direction of the engaging element in other element rows adjacent to the element row in the cross direction. In this case, although the above-mentioned lengthwise space regions in the machine direction are not provided in the molded surface fastener, it is possible to more effectively prevent the separation distances between the engaging pawl portions from becoming too large between the adjacent element rows in the cross direction, and therefore to more stably obtain appropriate peel strength and shear strength, etc.

In the molded surface fastener of the present invention, the engaging elements for each element row along the machine direction are formed such that the upper end surface or the upper end cross-section formed at a predetermined height position at the upper end part of each stem portion perpendicular to the standing direction of the stem portion (height direction of the engaging element) has the same shape and same area as each other. Further, in the plurality of the element rows, at least two types of element rows in which the areas of the upper end surfaces or the upper end cross-sections of the stem portions at the predetermined height position are different from each other are provided. In this case, it is preferable that the upper end surfaces or the upper end cross-sections of the stem portions are formed in a circular or oval shape.

As described above, at least two types of the element rows having different sizes in the direction perpendicular to the height direction of the engaging element are formed on the molded surface fastener, thereby, it is possible to complement the strengths and weaknesses of each of the engaging elements having each size. Therefore, the performance of the molded surface fastener can be less likely to be affected by the type of the non-woven fabric. In the present invention, the stem portions of all the engaging elements disposed in the plurality of element rows may be formed to have the same shape and the same size as each other.

In the present invention, as the element rows along the machine direction, at least first element rows in which the area of the upper end surface or the upper end cross section perpendicular to the standing direction in each of the stem portions is the first size and second element rows in which the area of the upper end surface or the upper end cross-section perpendicular to the standing direction in each of the stem portions is the second size to be larger than the first size are provided. Further, the first element rows and the second element rows are alternately arranged by one row in the cross direction. This makes it possible to more effectively complement the strengths and weaknesses of each of the engaging elements in the first element rows and the second element rows. As a result, the molded surface fastener can be formed so that the performance such as peel strength is less affected by the structure of the non-woven fabric and the like.

In this case, the upper end surface or the upper end cross-section in each of the stem portions in the first element rows and the upper end surface or the upper end cross section in each of the stem portions in the second element rows have a shape similar to each other. Further, the height dimension of each engage element in the first element rows from the base portion and the height dimension of each engaging element in the second element rows from the base portion are the same. Therefore, the feel (touch feeling) of the top surface of the molded surface fastener provided with the engaging elements can be improved, and the appearance quality (show) of the molded surface fastener can be enhanced.

Furthermore, in the molded surface fastener of the present invention, a set of the two symmetrical engaging pawl portions provided at symmetrical positions in the cross direction are, in the plan view of the engaging element, disposed at the middle part of the stem portion in the machine direction and protruded each other in opposite directions along the cross direction. Further, with respect to the engaging elements in each element row along the machine direction, the other element rows adjacent to the element row in the cross direction include two engaging elements in which the respective separation distances between the symmetrical engaging pawl portion of the element row and the symmetrical engaging pawl portion of the other element row are equal. Since the engaging elements are arranged in this manner, between the engaging elements in the element rows adjacent to the cross direction, it is possible to make the separation distances of the engaging pawl portions crossing the two element rows substantially the same size for all the engaging elements, and thus less likely to cause the difference in the ease of entering the loops.

Further, in the molded surface fastener of the present invention, since the engaging element pawl portions are formed to be sloped or curved downward toward the base portion, the loops of the loop member can be more easily caught in each engaging element, and therefore, the peel strength and the shear strength of the molded surface fastener can be more effectively enhanced.

MODES FOR CARRYING OUT THE INVENTION

Hereinafter, modes for carrying out the invention favorably will be described in detail showing embodiments with reference to the drawings. It should be noted that the present invention is not limited to the embodiments explained as below, and various changes can be made as long as having a substantially same structure and similar functional effects. In the following embodiments, for example, the number, the size (thickness and height), a forming density (size of pitch interval), and the like of the engaging elements disposed on the base portion of the molded surface fastener are not particularly limited, and can be changed arbitrarily.

Embodiment 1

Figure 1:
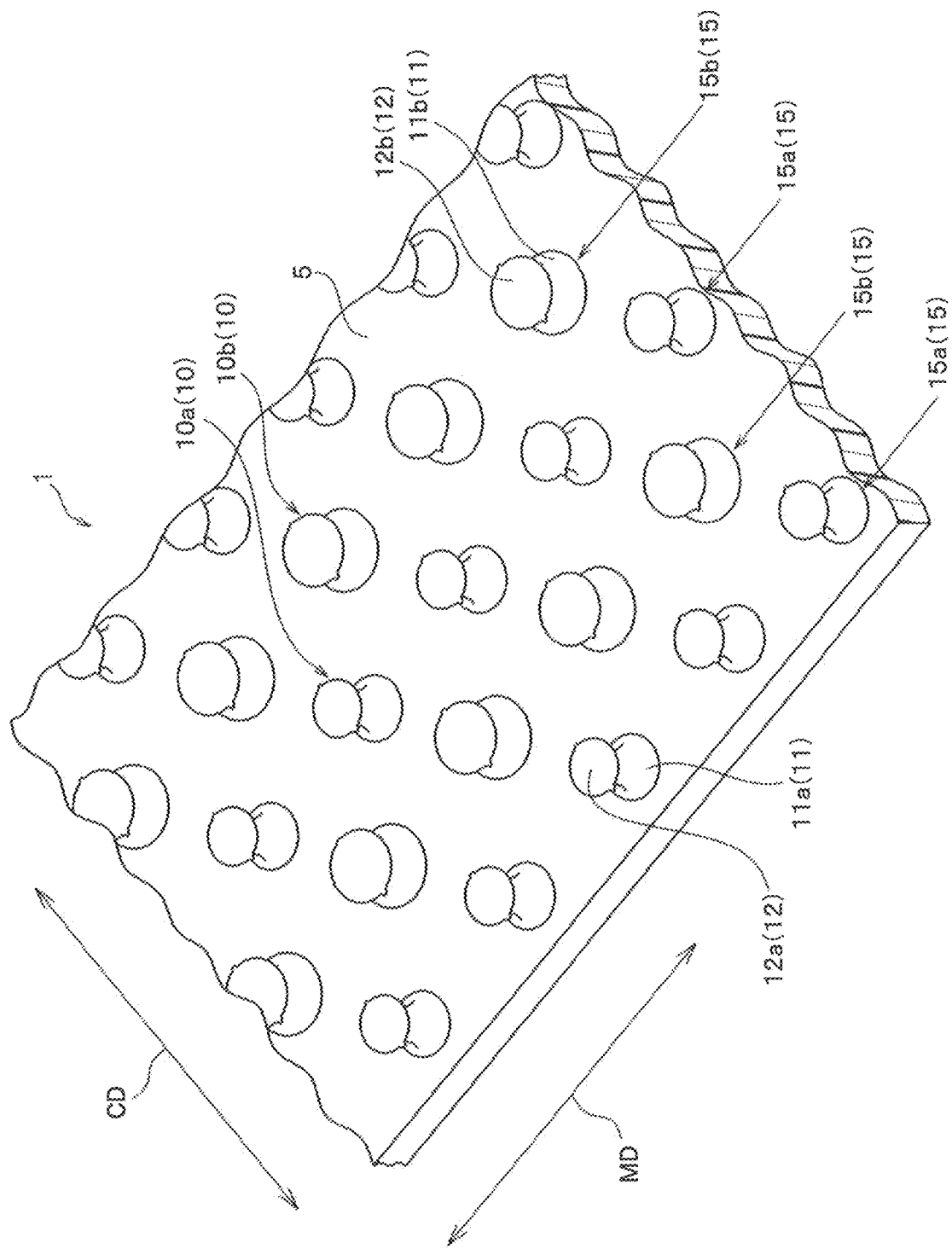
FIG. 1 is a perspective view illustrating a molded surface fastener according to Embodiment 1 of the present invention.
Figure 2:
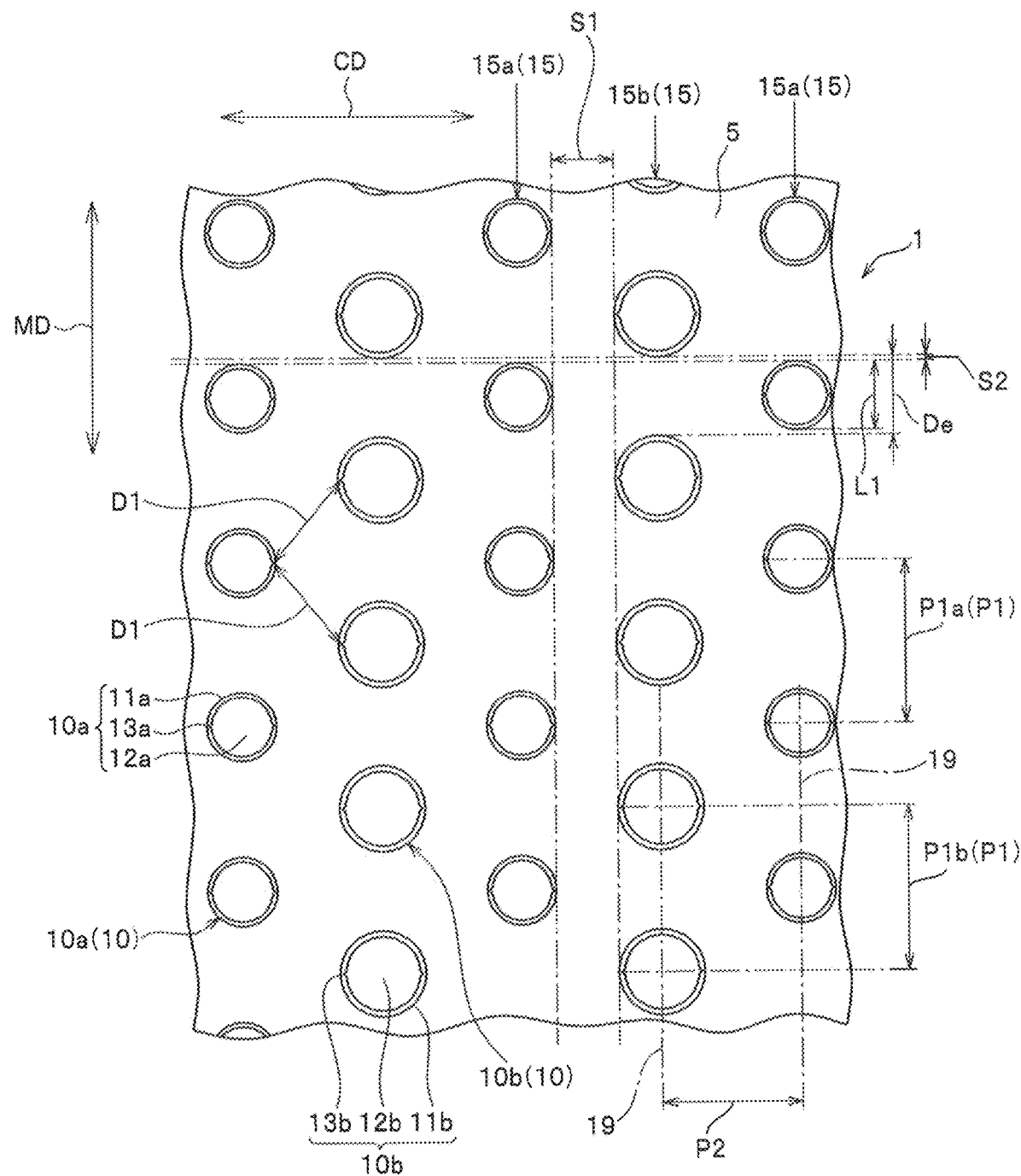
FIG. 2 is a plan view of the molded surface fastener.
Figure 3:
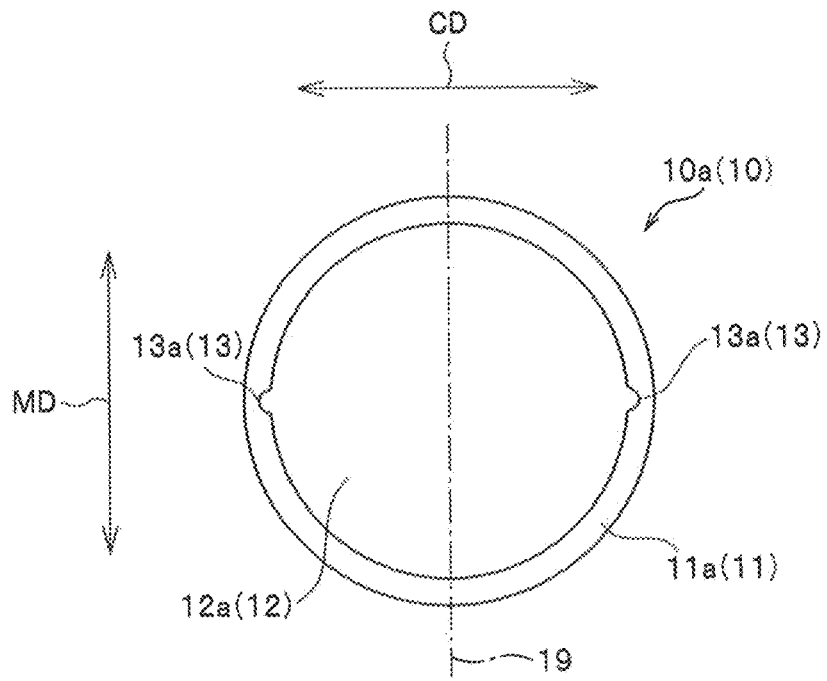
FIG. 3 is a plan view illustrating a first engaging element of the molded surface fastener.
Figure 4:
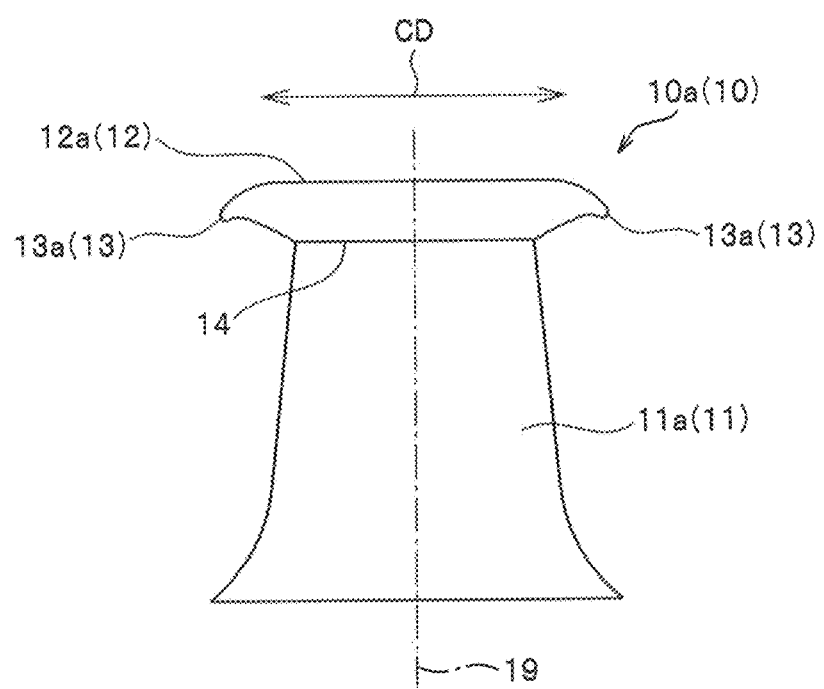
FIG. 4 is a front view of the first engaging element when viewed from a machine direction.
Figure 5:
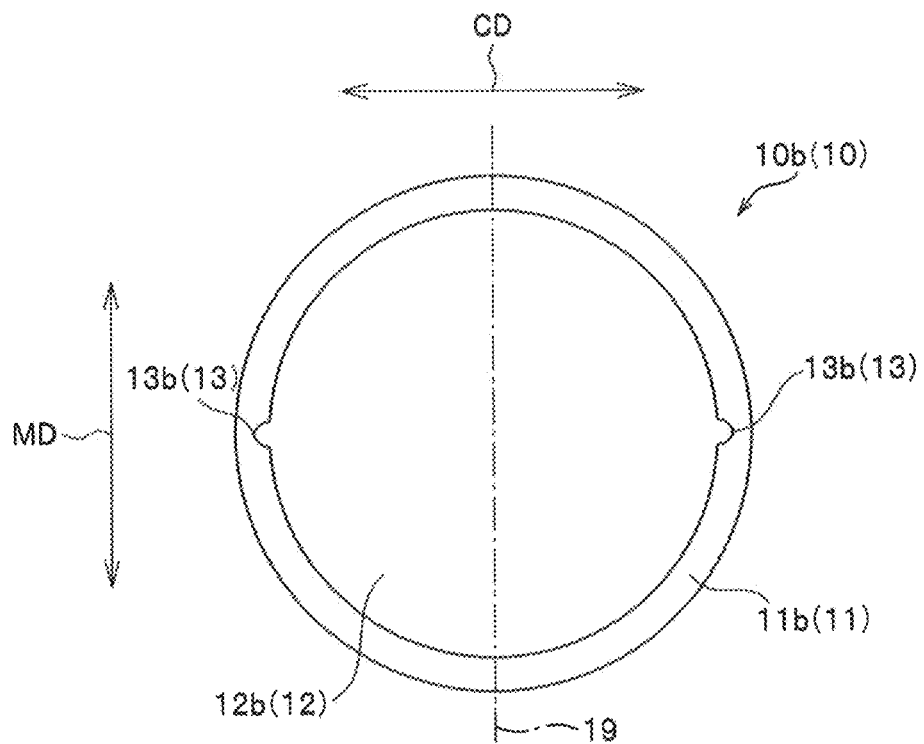
FIG. 5 is a plan view illustrating a second engaging element of the molded surface fastener.
Figure 6:
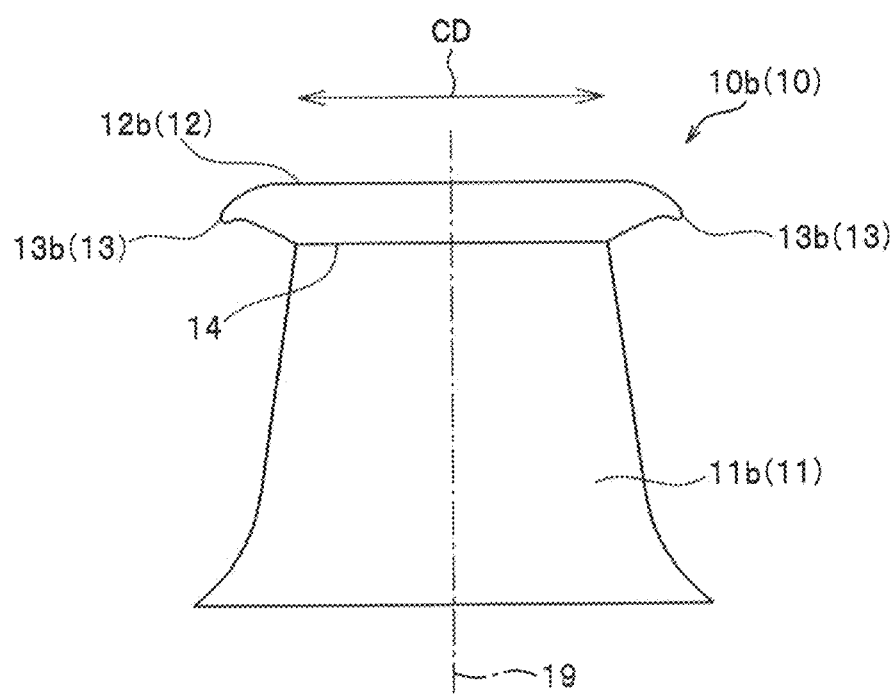
FIG. 6 is a front view of the second engaging element when viewed from the machine direction.

FIG. 1 is a perspective view illustrating a molded surface fastener according to Embodiment 1, and FIG. 2 is a plan view of the molded surface fastener. FIG. 3 and FIG. 4 are a plan view and a front view illustrating a first engaging element of the molded surface fastener enlarged. FIG. 5 and FIG. 6 are a plan view and a front view illustrating a second engaging element of the molded surface fastener enlarged.

In the following explanations, a front and rear direction regarding a molded surface fastener and a primary molded body is defined as a length direction of the molded surface fastener and the primary molded body which is to be molded as a long size, as described later, and as a first direction along a machine direction (M direction or MD) in which the molded surface fastener or the primary molded body is conveyed in a manufacturing step of the molded surface fastener.

A right and left direction is defined as a width direction perpendicular to the length direction and along an upper surface (or lower surface) of the base portion in the molded surface fastener. In this case, the right and left direction and the width direction can also be defined as a cross direction (C direction or CD) crossing to the machine direction (MD) or as a second direction. An upper and lower direction (thickness direction) is a height direction (height direction of an engaging element) perpendicular to the length direction and perpendicular to an upper surface (or lower surface) of the base portion in the molded surface fastener.

Figure 7:
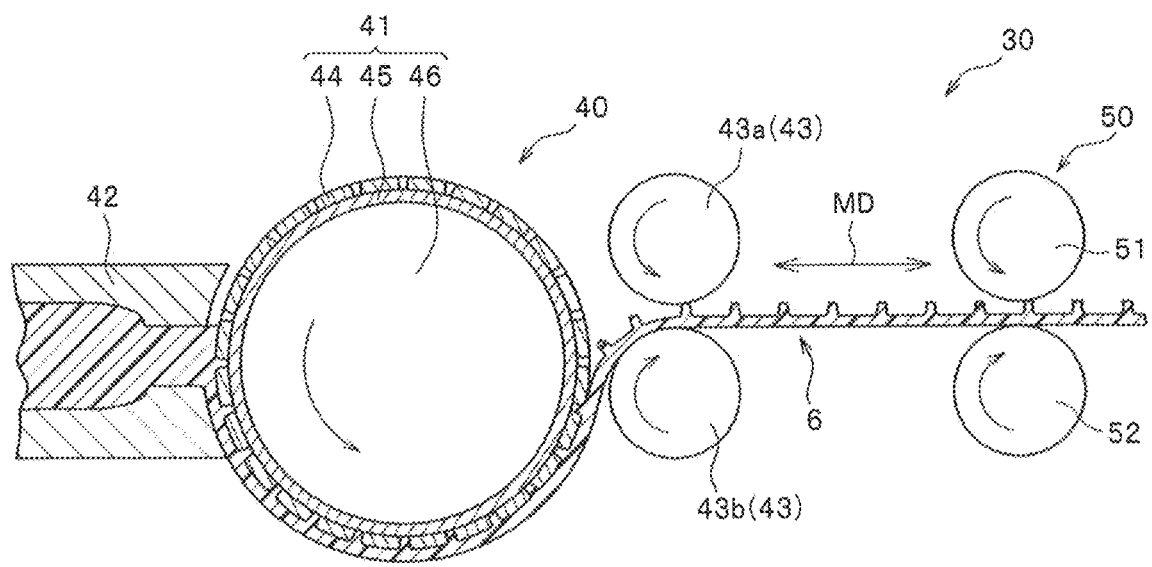
FIG. 7 is a schematic view schematically illustrating a manufacturing apparatus which manufactures the molded surface fastener.

The molded surface fastener 1 of Embodiment 1 shown in FIG. 1 and FIG. 2 is manufactured using a manufacturing apparatus 30 having a molding apparatus 40 and a heat press apparatus 50 as shown in FIG. 7 as described later. The molded surface fastener 1 is formed as a rectangular sheet shape to be long in a machine direction of the manufacturing apparatus 30 in a plan view. It should be noted that the length dimension and the width dimension of the molded surface fastener 1 of the present invention are not particularly limited, and can be arbitrarily changed by cutting the molded surface fastener 1. Further, it is possible that the molded surface fastener 1 has a shape other than a rectangle in the plan view.

The kinds of synthetic resin forming the molded surface fastener 1 are not particularly limited as well. As a material of the molded surface fastener 1, a thermoplastic resin such as polypropylene, polyester, nylon, polybutylene terephthalate, or a copolymer thereof can be adopted. In the case of Embodiment 1, the molded surface fastener 1 is made of polypropylene.

The molded surface fastener 1 of Embodiment 1 has a thin plate-shaped base portion 5 and a plurality of engaging elements 10 standing vertically on an upper surface of the base portion 5. The base portion 5 is formed to be long in the machine direction MD at the time of manufacturing. In addition, the base portion 5 is formed to have a predetermined thickness to be able to obtain appropriate strength, and the upper surface and a lower surface of the base portion 5 are flat and formed to be parallel to each other. On the upper surface of the base portion 5, a plurality of engaging elements 10 is provided to be aligned regularly in a staggered arrangement pattern as described later.

In Embodiment 1, the engaging elements 10 have first engaging elements 10a and second engaging elements 10b, each of which is formed to be thicker than the first engaging element 10a. The fact that the second engaging element 10b is thicker than the first engaging element 10a here means that, the second engaging element 10b is larger than the first engaging element 10a when the cross-sectional areas of a predetermined height position (for example, position of a boundary portion 14 between the stem portion 11 and an engaging head portion 12) in at least a stem portion 11, described later, of each engaging element 10, perpendicular to a height direction are compared.

Further, each engaging element 10 has a substantially truncated cone-shaped stem portion 11 standing on the base portion 5, a disk-shaped or a dish-shaped engaging head portion 12 formed to be bulged upward further from an upper end part of the stem portion 11 and to be projected outward from an entire periphery of the upper end part of the stem portion 11, and two micro engaging pawl portions 13 protruded outward from an outer peripheral edge part of the engaging head portion 12. This structure is common to the first engaging element 10a and the second engaging element 10b.

In this case, the stem portion 11, the engaging head portion 12, and the engaging pawl portions 13 in the first engaging element 10a are referred to as a first stem portion 11a, a first engaging head portion 12a, and a first engaging pawl portion 13a, and similarly in the second engaging element 10b, referred to as a second stem portion 11b, a second engaging head portion 12b, and a second engaging pawl portion 13b. Further, the engaging pawl portion 13 is simply expressed as a pawl portion in some cases.

In Embodiment 1, an upper end cross section at the upper end part of the stem portion 11 in the first engaging element 10a and the second engaging element 10b (in other words, the boundary portion 14 of the stem portion 11 and the engaging head portion 12) perpendicular to an upper and lower direction has a circular shape. In this case, the above-mentioned circular upper end cross-section in the first engaging element 10a and the circular upper end cross-section in the second engaging element 10b are in similarity relation to each other.

That is, the above-mentioned circular upper end cross-section in the first engaging element 10a has a predetermined first-sized area, and the above-mentioned circular upper end cross-section in the second engaging element 10b has a predetermined second-sized area which is larger than the first size as above. In the present invention, it is possible that the area of the circular cross-section (the first and second sizes as above) include an error of about ±20%. In this case, the area of the circular upper end cross-section of the stem portion 11 in the second engaging element 10b is 125% or larger and 250% or smaller, and preferably 150% or larger and 200% or smaller with respect to the area of the circular upper end cross-section of the stem portion 11 in the first engaging element 10a.

The first engaging element 10a formed to be thinner than the second engaging element 10b as mentioned above, for example, when a non-woven fabric (loop member) is engaged with the molded surface fastener 1, can be easily entered between the loops of the non-woven fabric compared to the second engaging element 10b. Therefore, the loops of the non-woven fabric can be engaged with the first engaging element 10a more easily. On the other hand, regarding the second engaging element 10b formed to be thicker than the first engaging element 10a, for example, when the non-woven fabric is engaged with the molded surface fastener 1, the loops can be hardly disengaged from the second engaging element 10b compared to the first engaging element 10a. Therefore, a state that the loops are caught by the second engaging element 10b (engaged state) can be held more stably.

Further, in Embodiment 1, the first engaging element 10a and the second engaging element 10b can be clearly distinguished since the second engaging element 10b indicates a larger value than the first engaging element 10a by comparing the area of the circular upper end cross-section at the upper end part (or the boundary portion 14) of the stem portion 11 as above as well as, for example, comparing the diameter or radius of the circular upper end cross-section at the upper end part (or the boundary portion 14) of the stem portion 11, the area of the circular engaging head portion 12 in the plan view of the engaging element 10, the diameter or radius of the circular engaging head portion 12 in the plan view of the engaging element 10 and the like.

The stem portion 11 of the engaging element 10 (first stem portion 11a and second stem portion 11b) is provided upright on the base portion 5, and has a truncated cone shape such that the cross-sectional area perpendicular to the upper and lower direction gradually increases as approaching to the base portion 5. Particularly, a lower end part of the stem portion 11 of Embodiment 1 is formed to be curved so that the outer peripheral surface expands downward. In the present invention, the shape of the stem portion 11 is not limited to a truncated cone shape, and may be, for example, a truncated pyramid shape such as a truncated square shape, a columnar shape, or a prismatic shape such as a square prism shape.

The engaging head portion 12 (first engaging head portion 12a and second engaging head portion 12b) has a disc shape, and is formed integrally on the stem portion 11 via the boundary portion 14. In the case of Embodiment 1, the engaging head portion 12 has a circular shape in the plan view when the engaging element 10 is viewed from above. The circular shape of the engaging head portion 12 in the plan view is a similar shape with the circular shape of the cross-section at the boundary portion 14 of the engaging element 10 perpendicular to the upper and lower direction (in other words, the upper end cross section at the upper end part of the stem portion 11 perpendicular to the upper and lower direction). It should be noted that the similarity referred to here includes the case that both shapes are completely matched as well as overlapped with each other in the area of 85% or larger, and preferably 90% or larger when the scale of one shape are enlarged or reduced to be overlapped so as to match the scale of the other shape.

The engaging head portion 12 is provided with a flat head portion top end surface disposed parallel to the upper surface of the base portion 5. Further, between the head portion top end surface and a head portion back surface disposed to be sloped from the upper end outer peripheral edge of the stem portion 11, an outer peripheral side surface in a curved surface-shaped is formed in the entire peripheral direction of the engaging head portion 12. In the present invention, since the shape of the engaging head portion 12 is related to the cross-sectional shape of the stem portion 11 perpendicular to the height direction, it is possible to have a shape other than the circular shape in the plan view depending on the shape of the stem portion 11.

A height dimension (a dimension in a height direction) of the first engaging element 10a from the upper surface of the base portion 5 to the head portion top end surface of the engaging head portion 12 and a height dimension of the second engaging element 10b from the upper surface of the base portion 5 to the head portion top end surface of the engaging head portion 12 are set to be the same size. Therefore, even when a plurality of the engaging elements 10 is provided on the upper surface (top surface) of the base portion 5, the upper surface (top surface) of the molded surface fastener 1 can have good feel and touch feeling.

Since the first engaging elements 10a and the second engaging elements 10b thicker than the first engaging elements 10a are regularly arranged as particularly in the case of Embodiment 1, the feel of the top surface of the molded surface fastener 1 can be improved, for example, as compared to the case that only the first engaging elements 10a are regularly arranged in the same way.

Each engaging element 10 of Embodiment 1 has two engaging pawl portions 13 protruded outward from a part the outer peripheral side surface of the engaging head portion 12. Further, the two engaging pawl portions 13 of each engaging element 10 are, in the plan view of the engaging element 10 (FIG. 3 and FIG. 5), when an imaginary center line 19 is drawn along the machine direction (length direction of the base portion 5) MD at a middle position of the cross direction (width direction of the base portion 5) in the stem portion 11 and the engaging head portion 12, provided as a pair of symmetrical engaging pawl portions 13 disposed at a position to be line-symmetrical with each other with respect to the imaginary center line 19.

In this case, a set of two engaging pawl portions 13 symmetrically disposed on each engaging element 10 are, in the plan view of the engaging element 10, protruded in opposite directions to each other in the cross direction (right and left direction) CD from a part of the outer peripheral side surface in the middle part of the engaging head portion 12 in the machine direction MD. Particularly in the case of Embodiment 1, only the pair of symmetrical engaging pawl portions 13 as above are provided in all the engaging elements 10 as an engaging pawl portion 13 protruded outward from a part of the outer peripheral side surface of the engaging head portion 12.

The right and left symmetrical engaging pawl portions 13 are formed to be protruded in the cross direction CD sides from a part of the engaging head portion 12, in other words, to be protruded outward so as to be along the cross direction CD from a part of the engaging head portion 12. The fact that the engaging pawl portion 13 is protruded in the cross direction CD side here means that regarding the cross direction CD, the engaging pawl portion 13 is formed such that with respect to a position of a base end part of the engaging pawl portion 13 connected to the engaging head portion 12, a position of a tapered tip end part of the engaging pawl portion 13 is disposed on an outer side in the cross direction CD (a side apart from a center position of the engaging head portion 12 in the cross direction CD).

Figure 11:
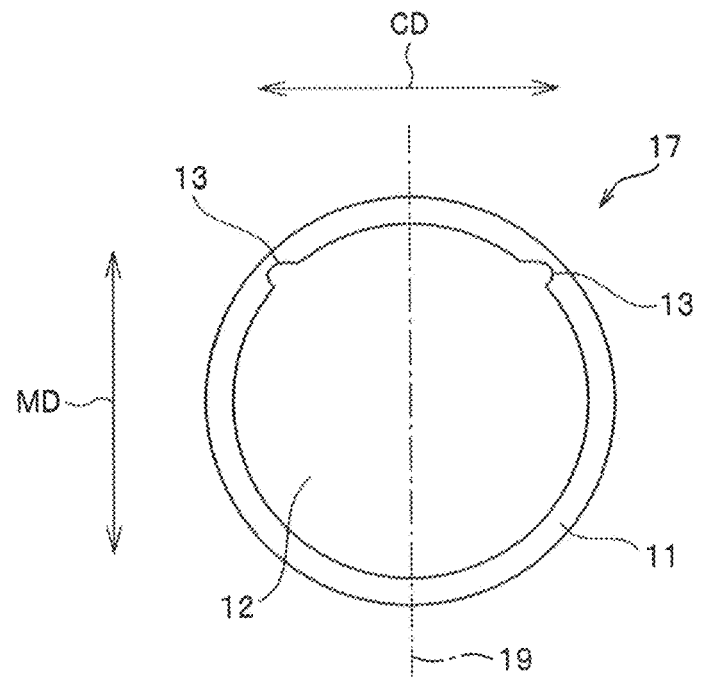
FIG. 11 is a plan view illustrating an engaging element according to a modification example of Embodiment 1.
Figure 12:
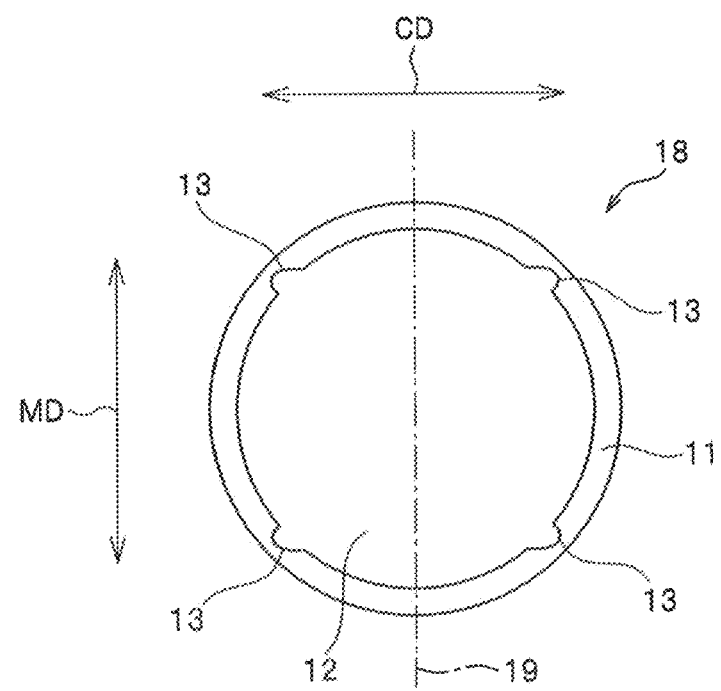
FIG. 12 is a plan view illustrating an engaging element according to another modification example of Embodiment 1.

In the engaging element of the present invention, at least a set of two symmetrical engaging pawl portions 13 may be provided at positions to be line-symmetrical with each other with respect to the above-mentioned imaginary center line 19 in the plan view of the engaging element. For example, in the present invention, it is possible that a pair of symmetrical engaging pawl portions 13 are not provided at the above-mentioned middle part position of the engaging head portion 12 in the machine direction MD, and a pair of symmetrical engaging pawl portions 13 are provided at the position symmetrical about the cross direction CD of one end part (or the other end part) in the machine direction MD of the engaging head portion 12 in the engaging element 17, for example, as a modification example of the engaging element is shown in FIG. 11. Further, although not shown, it is possible that a pair of symmetrical engaging pawl portions and other engaging pawl portions are provided with respect to one engaging element, and that two sets of two symmetrical engaging pawl portions 13 symmetrical about the cross direction CD are provided in the engaging element 18, for example, as another modification example of the engaging element is shown in FIG. 12.

In the present Embodiment 1, each engaging pawl portion 13 is formed to be sloped or curved downward toward the base portion 5, and has a shape hanging downward toward the tip end like a bird's claws. That is, one engaging pawl portion 13 has an upper surface which is sloped downward toward the tip end, a back surface (lower surface) disposed facing to the base portion 5, and a pair of side wall surfaces disposed between the upper surface and the back surface. Each engaging pawl portion 13 serves as an engaging portion which maintains engagement by being caught in the loops of the loop member when the engaging elements 10 are entered into the loop member which is to be an engaging counterpart such as a non-woven fabric.

In this case, in the base end part of the engaging pawl portion 13 connected to the engaging head portion 12, a width dimension between the pair of side wall surfaces of the engaging pawl portion 13 is set to be the size of ⅓ or smaller, preferably ⅕ or smaller, and further preferably ⅐ or smaller of the dimension in the machine direction MD of the above-mentioned boundary portion 14 in the engaging element 10. Thereby, the engaging pawl portions 13 that contribute to the improvement of the engaging strength (peel strength) of the molded surface fastener 1 can be stably provided at the outer peripheral edge part of the engaging head portion 12, and the influence of the engaging pawl portion 13 on the touch feeling of the molded surface fastener 1 can be reduced.

In Embodiment 1, the first engaging pawl portion 13*a* provided on the first engaging element 10*a* and the second engaging pawl portion 13*b* provided on the second engaging element 10*b* are formed to be the same size (or substantially the same size) as each other. For example, the width dimension at the base end part of the first engaging pawl portion 13*a* and the second engaging pawl portion 13*b* are same size as each other (including an error of about ±20%). In Embodiment 1, it is also possible to form the first engaging element 10*a* and the second engaging element 10*b* to have different sizes from each other in the first engaging pawl portion 13*a* of the first engaging element 10*a* and the second engaging pawl portion 13*b* of the second engaging element 10*b*. Furthermore, in the present invention, the shape of the engaging pawl portion 13 itself is not particularly limited, and can be arbitrarily changed.

In the molded surface fastener 1 of Embodiment 1, a plurality of engaging elements 10 (first engaging element 10*a* and second engaging element 10*b*) are arranged in a line at a predetermined (constant) pitch interval P1 along the machine direction MD, thereby an element row (MD element row) 15 is formed linearly. In this case, the element rows 15 of Embodiment 1 have a first element rows 15*a* formed of a plurality of first engaging elements 10*a* and the second element rows 15*b* formed of a plurality of second engaging elements 10*b*.

Furthermore, a pitch interval P1*a* in the machine direction MD of the first engaging elements 10*a* forming the first element row 15*a* and a pitch interval P1*b* in the machine direction MD of the second engaging elements 10*b* forming the second element row 15*b* are set to be the same length. The pitch interval P1 in the machine direction MD of the engaging elements 10 here is, in the plan view (FIG. 2) of the molded surface fastener 1, defined as an interval (shortest distance) from a predetermined position (for example, center position in the machine direction MD of the engaging element 10) of the engaging element 10 to a predetermined position of an engaging element 10 adjacent to the engaging element 10 in the machine direction MD.

Furthermore, the first element rows 15*a* and the second element rows 15*b* are alternately placed one by one in the cross direction CD and are formed in parallel with each other. In particular, the first element rows 15*a* and the second element rows 15*b* are alternately disposed at a predetermined pitch interval P2 in the cross direction CD. In Embodiment 1, the pitch interval P2 in the cross direction CD of the element rows 15 is defined as an interval (shortest distance) between the straight line connecting the center positions in the cross direction CD in the plurality of first engaging elements 10*a* forming the first element row 15*a* and the straight line connecting the center positions in the cross direction CD in the plurality of second engaging elements 10*b* forming the second element row 15*b*.

In the case of Embodiment 1, the pitch interval P2 in the cross direction CD between the element rows 15 is set to be slightly smaller than the pitch interval P1 in the machine direction MD between the engaging elements 10 in each element row 15. In the present invention, it is possible that the pitch interval P2 in the cross direction CD between the element rows 15 is set to be the same size as, or set to be larger than the pitch interval P1 in the machine direction MD between the engaging elements 10 in each element row 15 depending on the application of the molded surface fastener 1 and the like.

Further, in the molded surface fastener 1 of Embodiment 1, the first engaging elements 10a forming the first element rows 15a and the second engaging elements 10b forming the second element rows 15b are, regarding the positions in the machine direction MD, arranged to be shifted each other by half the size of the pitch interval P1 in the machine direction MD between the engaging elements 10 in the element row 15.

That is, each first engaging element 10a in the first element rows 15a is, in the machine direction MD, disposed at a position corresponding to a center position between the two second engaging elements 10b adjacent to each other in the machine direction MD in the second element row 15b with respect to the second engaging elements 10b in the second element rows 15b. Further, each second engaging element 10b in the second element rows 15b is, in the machine direction MD, disposed at a position corresponding to a center position between the two first engaging elements 10a adjacent to each other in the machine direction MD in the first element row 15a with respect to the first engaging elements 10a in the first element rows 15a.

Therefore, the first engaging elements 10a and the second engaging elements 10b are arranged on the base portion 5 in a staggered (or zigzag) pattern to be alternately positioned at a predetermined interval in the machine direction MD. In this case, a protruding direction (cross direction CD) of the pair of symmetrical engaging pawl portions 13 provided in each engaging element 10 and a direction (machine direction MD) for shifting the position of the engaging element 10 between the first element row 15a and the second element row 15b has a relationship perpendicular to each other.

Since the first engaging elements 10a and the second engaging elements 10b are arranged regularly in a staggered positional relationship as above, it is possible to manage easily forming positions of the first engaging elements 10a and the second engaging elements 10b at the time of manufacturing the molded surface fastener 1, and to suppress the decrease in yield due to occurrence of a dimension error or the like.

By adopting the staggered pattern as an arrangement of the first engaging elements 10a and the second engaging elements 10b, as shown in FIG. 2, in the first element rows 15a and the second element rows 15b adjacent to each other in the cross direction CD, a separation distance D1 between the first engaging pawl portion 13a provided in one side in the cross direction CD of the first engaging element 10a and the second engaging pawl portion 13b provided in the other side in the cross direction CD of the second engaging element 10b can be made the same size in any combination of the first engaging elements 10a and the second engaging elements 10b adjacent to each other.

In this case, for each first engaging element 10a in the first element rows 15a, there are two second engaging elements 10b having the same separation distance D1 between the first engaging pawl portion 13a and the second engaging pawl portion 13b, described above, in the second element row 15b adjacent to the first element row 15a. Similarly, for each second engaging element 10b in the second element rows 15b, there are two first engaging elements 10a having the same separation distance D1 as above in the adjacent first element row 15a.

In the molded surface fastener 1 of Embodiment 1, between the first element row 15a and the second element row 15b adjacent to each other in the cross direction CD, a widthwise space region S1 in the cross direction CD in which the first engaging element 10a and the second engaging element 10b are not provided is provided. The widthwise space region S1 in the cross direction CD is formed linearly and continuously along the machine direction MD. The widthwise space region S1 is a region in which the stem portion 11 is not protruded on the base portion 5, and the first engaging element 10a and the second engaging element 10b are not overlapped, therefore, when the loop member is engaged with the molded surface fastener 1, many loops of the loop member can be easily and smoothly entered therein.

In this case, the pitch interval P2 in the cross direction CD between the element rows 15 is set to be larger than the half size of the pitch interval P1 in the machine direction MD between the engaging elements 10 in each element row 15. By setting the pitch interval P2 to be larger than the predetermined size in this manner, the dimension (width dimension) in the cross direction CD of the above-mentioned widthwise space region S1 can be made large to form the widthwise space region S1 to be wide in the cross direction CD. Thus, the loops of the loop member can be more easily entered into the widthwise space region S1.

Further in Embodiment 1, as shown in FIG. 2, when a minimum value of the distance between the second engaging elements 10b adjacent to each other in the machine direction MD in the second element row 15b is referred to as a minimum element separation distance De of the second element row 15b, the minimum element separation distance De in the second element row 15b is set to be larger than a maximum value (maximum dimension in the machine direction MD) L1 of the dimension in the machine direction MD of each first engaging element 10a in the first element row 15a. Similarly, when a minimum value of the distance between the first engaging elements 10a adjacent to each other in the machine direction MD in the first element row 15a is referred to as a minimum element separation distance in the first element row 15a, the minimum element separation distance in the first element row 15a is set to be larger than a maximum dimension in the machine direction MD of each second engaging element 10b in the second element row 15b.

By setting the minimum element separation distance in the first element row 15a and the minimum element separation distance De in the second element row 15b as mentioned above, in the plan view when the molded surface fastener 1 is viewed from above, the lengthwise space regions S2 in the machine direction MD in which the first engaging elements 10a and the second engaging elements 10b are not provided can be provided over the entire molded surface fastener 1 in the cross direction CD. In this case, the lengthwise space region S2 in the machine direction MD is formed linearly and continuously along the cross direction CD as a region in which the stem portion 11 is not protruded on the base portion 5, and the first engaging element 10a and the second engaging element 10b are not overlapped.

A dimension in the machine direction MD of the lengthwise space region S2 is set to be smaller than the dimension in the cross direction CD of the widthwise space region S1 as above. By making the dimension in the machine direction MD of the lengthwise space region S2 small in this manner, in the first element rows 15a and the second element rows 15b, it is possible to prevent that the above-mentioned separation distance D1 between the first engaging pawl portion 13a and the second engaging pawl portion 13b becomes too long (the first engaging pawl portion 13a and the second engaging pawl portion 13b are too far apart). Therefore, since the loops of the loop member that has entered between the first engaging pawl portion 13a and the second engaging pawl portion 13b can be engaged effectively, appropriate peel strength and shear strength for the loop member of the molded surface fastener 1 can be stably secured.

In Embodiment 1, the minimum element separation distance De in the second element row 15b is larger than a maximum dimension L1 in the machine direction MD of the first engaging element 10a and the minimum element separation distance in the first element row 15a is larger than the maximum dimension in the machine direction MD of the second engaging element 10b as mentioned above, thereby the lengthwise space region S2 is provided. In the present invention, however, it is also possible to set each minimum element separation distance in the second element row 15b and the first element row 15a to be equal to or smaller than the maximum dimension in the machine direction MD of the first engaging element 10a and the second engaging element 10b.

For example, each minimum element separation distance in the second element row 15b and the first element row 15a is the same size as the maximum dimension in the machine direction MD of the first engaging element 10a and the second engaging element 10b, thereby, the above-mentioned lengthwise space region S2 is not provided. Therefore, the first engaging elements 10a and the second engaging elements 10b can be arranged in a positional relationship in which one end part in the machine direction MD of the first engaging element 10a and the other end part in the machine direction MD of the second engaging element 10b are in contact with one imaginary straight line which is parallel to the cross direction CD.

Further, each minimum element separation distance in the second element row 15b and the first element row 15a is smaller than the maximum dimension in the machine direction MD of the first engaging element 10a and the second engaging element 10b, thereby, the lengthwise space region S2 is not provided. Therefore, the first engaging elements 10a and the second engaging elements 10b can be arranged in a positional relationship in which a part of the first engaging element 10a and a part of the second engaging element 10b are overlapped in a side view when the molded surface fastener 1 is viewed from right and left sides.

Furthermore, each minimum element separation distance in the second element rows 15b and the first element rows 15a is set to be respectively equal to or smaller than the maximum dimension in the machine direction MD of the first engaging element 10a and the second engaging element 10b, thereby, in the first element rows 15a and the second element rows 15b, it is possible to more effectively prevent the above-mentioned separation distance D1 between the first engaging pawl portion 13a and the second engaging pawl portion 13b from becoming too long.

The molded surface fastener 1 having the above-mentioned structure in Embodiment 1 is manufactured by using a manufacturing apparatus 30 as shown in FIG. 7.

The manufacturing apparatus 30 has a molding apparatus 40 for conducting a primary molding step and a heat press apparatus 50 for heating a primary molded body 6 molded by the primary molding step as well as pressing a part of the primary molded body 6.

The molding apparatus 40 in Embodiment 1 has a die wheel 41 rotating and driving in one direction (counterclockwise direction in the drawings), an extrusion nozzle 42 which is disposed to face a peripheral surface of the die wheel 41 and extruding continuously a molten synthetic resin material, and a pickup roller 43 disposed on a downstream side of the extrusion nozzle 42 in a rotation direction of the die wheel 41.

The die wheel 41 is provided with an outer side cylindrical body (outside sleeve) 44 in a cylindrical shape to be a mold member, an inner side cylindrical body (inside sleeve) 45 in a cylindrical shape disposed in close contact with an inside of the outer side cylindrical body 44, and a rotation driving roller 46 for rotating the outer side cylindrical body 44 and the inner side cylindrical body 45 in one direction.

The die wheel 41 can rotate the outer side cylindrical body 44 and the inner side cylindrical body 45 concentrically by the rotation driving roller 46. Further, a cooling jacket (not shown) for circulating cooling liquid is provided inside the rotation driving roller 46, so that the primary molded body 6 molded on the peripheral surface of the die wheel 41 can be efficiently cooled.

Figure 8:
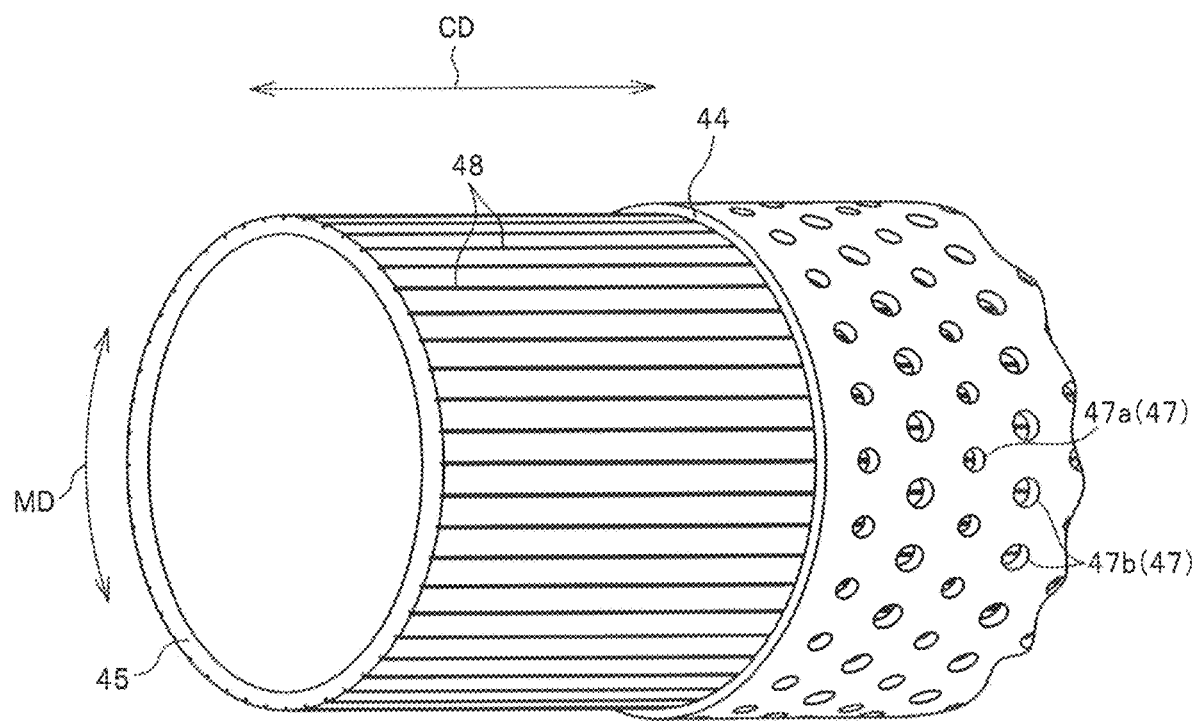
FIG. 8 is a perspective view schematically illustrating an outer side cylindrical body and an inner side cylindrical body disposed on a molding apparatus of the manufacturing apparatus.
Figure 9:
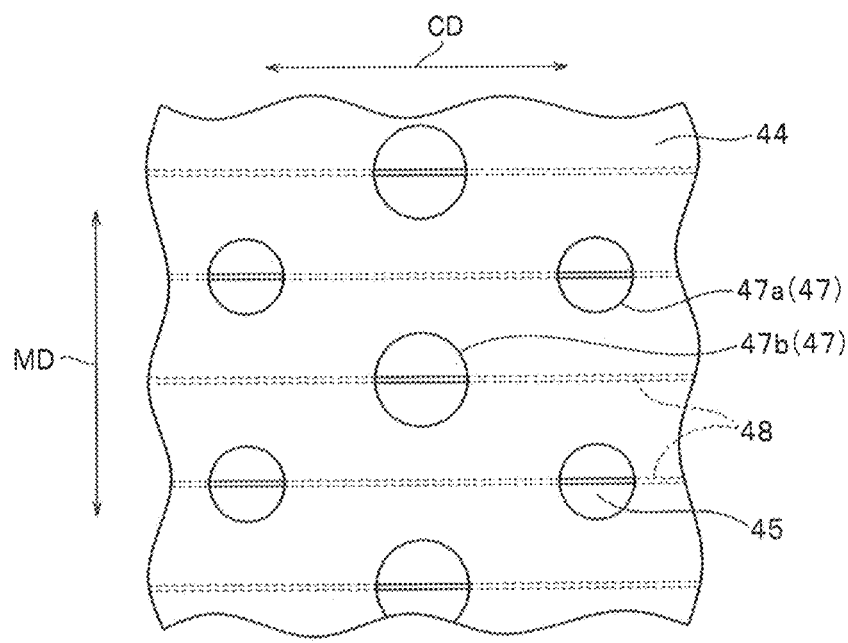
FIG. 9 is a schematic view schematically illustrating a positional relationship between a penetration hole formed on the outer side cylindrical body and a grooved channel portion provided on the inner side cylindrical body.

As shown in FIG. 8 and FIG. 9, a plurality of penetration holes 47 penetrating from an outer peripheral surface to an inner peripheral surface of the outer side cylindrical body 44 are provided on the outer side cylindrical body 44 of the die wheel 41 as cavities for molding provisional stem portions 21, descried later, of the primary molded body 6. The plurality of penetration holes 47 is formed corresponding to the arrangement position of the engaging elements 10 of the molded surface fastener 1 to be manufactured. Further, each of the penetration holes 47 has a substantially truncated cone shape in which a circular shape on the outer peripheral surface of the outer side cylindrical body 44 is formed larger than a circular shape on the inner peripheral surface of the outer side cylindrical body 44.

The penetration holes 47 on the outer side cylindrical body 44 have a first penetration hole 47a for molding a provisional stem portion 21 for the first engaging element 10a, and a second penetration hole 47b for molding a provisional stem portion 21 for the second engaging element 10b. The second penetration hole 47b is formed to have a larger inner diameter than that of the first penetration hole 47a. Further, the first penetration holes 47a and the second penetration holes 47b on the outer side cylindrical body 44 are formed in a staggered pattern corresponding to the staggered arrangement pattern of the first engaging element 10a and the second engaging element 10b of the molded surface fastener 1.

That is, the first penetration holes 47a and the second penetration holes 47b are respectively drilled on the outer side cylindrical body 44 in a predetermined interval along the machine direction MD (peripheral direction of the outer side cylindrical body 44), and forming rows of the first penetration holes 47a and forming rows of the second penetration holes 47b are provided alternately in the cross direction CD (axis direction of the outer side cylindrical body 44). Furthermore, the first penetration holes 47a and the second penetration holes 47b are, between the forming rows adjacent to each other, provided in shifted positions from each other by a half size of the predetermined interval in the machine direction MD as well as a smaller size than the pitch interval P2 in the cross direction CD between the element rows 15. In the present invention, the material and size of the outer side cylindrical body 44 and the inner side cylindrical body 45, and the method of forming them are not particularly limited.

A plurality of grooved channel portions 48 is formed on the outer peripheral surface of the inner side cylindrical body 45. Each of the grooved channel portions 48 are drilled linearly along the cross direction CD parallel to a central axis of the inner side cylindrical body 45 with a size capable of allowing the molten synthetic resin to flow in. Further, each of the grooved channel portions 48 on the inner side cylindrical body 45 is, as shown in FIG. 9, formed in the machine direction MD (peripheral direction) in a predetermined interval (predetermined pitch) corresponding to forming intervals of the first penetration holes 47a and the second penetration holes 47b so as to overlap the positions of diameters of the first penetration hole 47a and the second penetration hole 47b formed on the outer side cylindrical body 44.

Particularly in this case, an interval for forming the grooved channel portions 48 on the inner side cylindrical body 45 (i.e., a dimension in the machine direction MD from a center position in the machine direction MD of the grooved channel portion 48 to a center position in the machine direction MD of the adjacent grooved channel portion 48) corresponds to a half size of the forming interval of the first penetration holes 47a (length in the machine direction MD from a center position of the first penetration hole 47a to a center position of the adjacent first penetration hole 47a), and corresponds to a half size of the forming interval of the second penetration holes 47b.

The pickup roller 43 of the molding apparatus 40 has a pair of upper side holding roller 43a and lower side holding roller 43b for holding and pulling the primary molded body 6 molded on the peripheral surface part of the die wheel 41 from upper and lower sides. The upper side holding roller 43a and the lower side holding roller 43b are disposed to face each other with a predetermined interval. In addition, a surface layer (not shown) made of an elastomer such as polyurethane elastomer is provided on each of the outer peripheral surface part of the upper side holding roller 43a and the lower side holding roller 43b.

The upper side holding roller 43a and the lower side holding roller 43b of the pickup roller 43 rotate respectively in a predetermined direction at a predetermined speed, thereby the primary molded body 6 can be conveyed smoothly to the downstream side while continuously being peeled off from the die wheel 41.

The heat press apparatus 50 in Embodiment 1 has a pair of upper side press roller (upper side calender roller) 51 and lower side press roller (lower side calender roller) 52. The upper side press roller 51 and the lower side press roller 52 are disposed to face each other with a predetermined interval. In this case, an interval between the upper side press roller 51 and the lower side press roller 52 can be adjusted by a height adjusting means (not shown).

The upper side press roller 51 is provided with a heating source (not shown) inside, and disposed so as to rotate counterclockwise in FIG. 7. An outer peripheral surface of the upper side press roller 51 becomes a part heating and pressing a provisional element 20, described later, of the primary molded body 6 molded in the primary molding step from above. The lower side press roller 52 is disposed so as to rotate clockwise in FIG. 7, and supports the primary molded body 6 to be conveyed from below.

Figure 10:
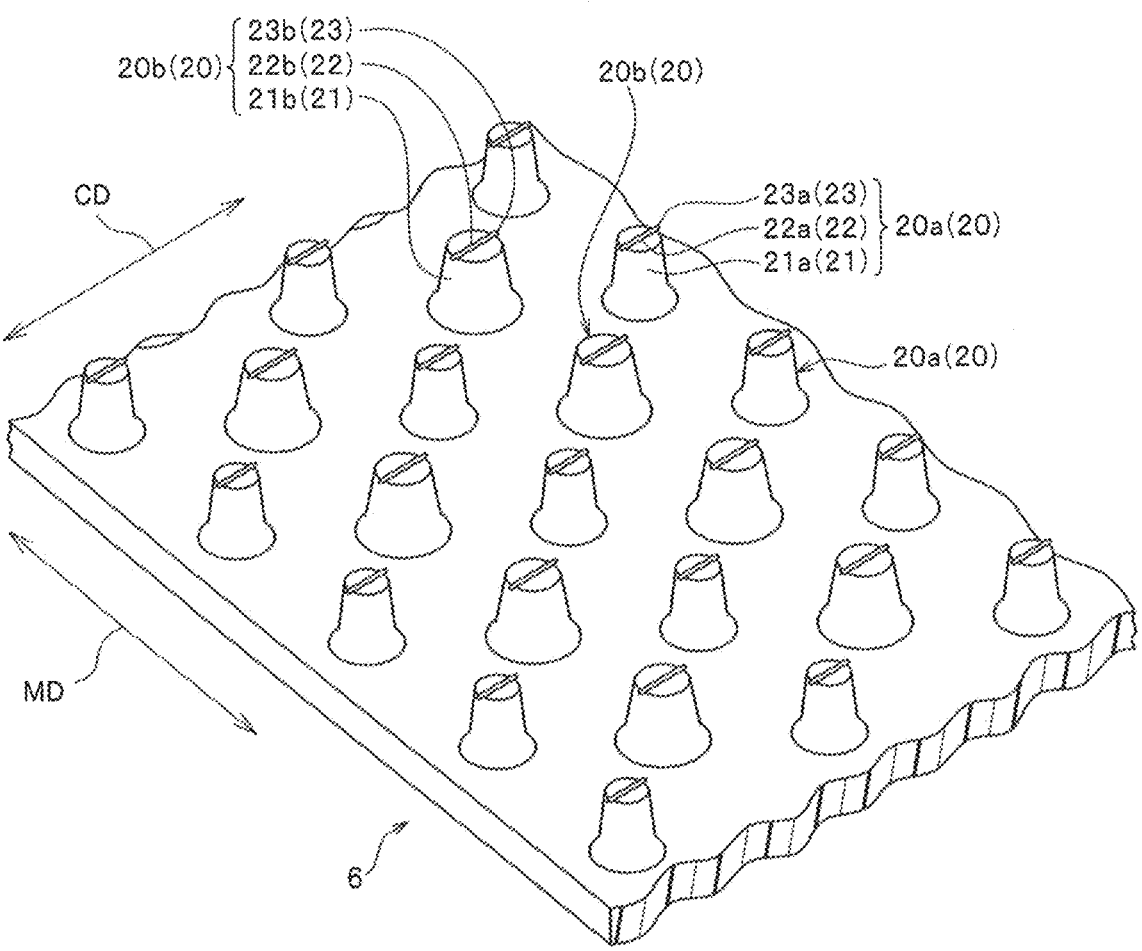
FIG. 10 is a perspective view illustrating a primary molded body molded with the molding apparatus.

In a case of manufacturing the molded surface fastener 1 using the manufacturing apparatus 30 having the molding apparatus 40 and the heat press apparatus 50 as described above, firstly, the primary molding step for molding the primary molded body 6 is conducted by the molding apparatus 40. In the primary molding step, the molten synthetic resin material is continuously extruded from the extrusion nozzle 42 toward the outer peripheral surface of the die wheel 41. Thereby, the primary molded body 6 as shown in FIG. 10 is molded on the outer peripheral surface part of the die wheel 41.

The primary molded body 6 molded in the primary molding step has a thin plate-shaped base portion 5 and a plurality of provisional elements 20 standing on the upper surface of the base portion 5. The base portion 5 of the primary molded body 6 becomes the base portion 5 of the molded surface fastener 1 as it is. The provisional element 20 is a part to be the engaging element 10 of the molded surface fastener 1 by being press-molded by the heat press apparatus 50 in a secondary molding step, described later.

The provisional elements 20 in Embodiment 1 have a first provisional elements 20a molded to be the first engaging elements 10a and a second provisional elements 20b molded to be the second engaging elements 10b. The second provisional element 20b is formed to have a thicker provisional stem portion 21, described later, than that of the first provisional element 20a. Each of the provisional elements 20 has a substantially truncated cone-shaped provisional stem portion 21 standing on the base portion 5, a rib portion 22 protruded on an upper surface of the provisional stem portion 21, and right and left provisional pawl portions (provisional engaging pawl portions) 23 protruded continuously from both right and left end edges of the rib portion 22 and substantially in parallel with the upper surface of the base portion 5 so as to project to an outside of the provisional stem portion 21. In this case, each of the provisional stem portions 21, the rib portions 22, and the provisional pawl portions 23 in the first provisional element 20a and the second provisional element 20b are referred to as a first provisional stem portion 21a and a second provisional stem portion 21b, a first rib portion 22a and a second rib portion 22b, and a first provisional pawl portion 23a and a second provisional pawl portion 23b.

The provisional stem portion 21 of the primary molded body 6 is molded by filling the penetration holes 47 provided on the outer side cylindrical body 44 with the synthetic resin in a molten state in the primary molding step. In the primary molding step, the rib portions 22 and the right and left provisional pawl portions 23 of the primary molded body 6 are formed by flowing the synthetic resin in a molten state from the penetration holes 47 of the outer side cylindrical body 44 into the grooved channel portions 48 provided on the inner side cylindrical body 45, and further to be entered into a part exceeding the penetration holes 47 along the grooved channel portions 48.

In this case, the rib portions 22 and the right and left provisional pawl portions 23 are formed along the cross direction CD. Further, the first rib portion 22a and the first provisional pawl portions 23a in each first provisional element 20a and the second rib portion 22b and the second provisional pawl portions 23b in each second provisional element 20b are formed by flowing the synthetic resin in a molten state into the grooved channel portions 48 having the same size, and therefore formed to be substantially the same size as each other.

Furthermore, the first provisional elements 20a and the second provisional elements 20b of the primary molded body 6 are arranged on the base portion 5 in the staggered pattern having an alternating positional relationship in the machine direction MD at a predetermined interval in the same manner as the arrangement of the first engaging elements 10a and the second engaging elements 10b in the molded surface fastener 1 described above.

The primary molded body 6 molded in the primary molding step is obtained by half-rotating the synthetic resin in a molten state extruded from the extrusion nozzle 42 to cure the synthetic resin while being supported on the outer peripheral surface part of the die wheel 41 and being cooled. Thereafter, the molded primary molded body 6 is continuously peeled off from the outer peripheral surface of the die wheel 41 by the pickup roller 43. At this time, the provisional pawl portions 23 of the primary molded body 6 are smoothly extracted from the grooved channel portions 48 on the inner side cylindrical body 45 and the penetration holes 47 on the outer side cylindrical body 44 while being elastically deformed.

Further, in the pickup roller 43, immediately after the molded surface fastener 1 is peeled off from the die wheel 41, the primary molded body 6 is conveyed to the downstream side while being held between the upper side holding roller 43a and the lower side holding roller 43b. At this time, even in a case that, for example, the primary molded body 6 is peeled off forcibly from the die wheel 41, thereby the provisional pawl portions 23 of the provisional element 20 in the primary molded body 6 are formed to be curved or bent diagonally upward, the provisional pawl portions 23 of the provisional element 20 can be deformed by being pressed by the upper side holding roller 43a so as to protrude parallel to the upper surface of the base portion 5 or downward toward the base portion 5.

Subsequently, the primary molded body 6 peeled off from the die wheel 41 is conveyed toward the heat press apparatus 50 that performs the secondary molding step, and introduced between the upper side press roller 51 and the lower side press roller 52 of the heat press apparatus 50. In the secondary molding step, each of the provisional elements 20 of the primary molded body 6 is pressed from above by the upper side press roller 51, and an upper end part of the provisional element 20 is squashed. Thereby, an upper end part of the provisional stem portion 21, the rib portion 22, and the provisional pawl portions 23 of each provisional element 20 are thermally deformed to mold the engaging head portion 12 and the right and left pair of engaging pawl portions 13 protruded from the outer peripheral side surface of the engaging head portion 12. Thus, the molded surface fastener 1 in Embodiment 1 as shown in FIG. 1 is manufactured.

Thereafter, the manufactured molded surface fastener 1 elongated in the machine direction MD is wound into a roll on a collecting roller or the like to be collected, or is conveyed toward a cutting part (not shown), cut to a predetermined width dimension and/or length dimension in the cutting part, and collected.

In the present invention, the manufacturing method, manufacturing conditions, and the like of the molded surface fastener 1 are not particularly limited, and can be arbitrarily changed.

In the molded surface fastener 1 of Embodiment 1 manufactured as above, the right and left pair of engaging pawl portions 13 are provided on the engaging head portion 12 of each engaging element 10, and the pair of engaging pawl portions 13 are protruded along the cross direction CD from symmetrical positions of the engaging head portion 12. Thereby, the molded surface fastener 1 in Embodiment 1, for example, when the non-woven loops that become the female surface fastener are engaged, the non-woven fabric loops can be easily caught on the engaging pawl portions 13 of each engaging element 10 and the loops can be less likely to be disengaged from each engaging element 10. Thus, high peel strength with respect to the non-woven fabric can be easily obtained.

Further, in the molded surface fastener 1 of Embodiment 1, since the first engaging elements 10a and the second engaging elements 10b are arranged regularly on the base portion 5 in the staggered pattern as mentioned above, as shown in FIG. 2, the separation distance D1 between the first engaging pawl portion 13a and the second engaging pawl portion 13b disposed so as to extend between the first element row 15a and the second element row 15b adjacent to each other can be made to have the same size for all the first engaging elements 10a and the second engaging elements 10b.

Thereby, when the loops of the non-woven fabric enter between the first element row 15a and the second element row 15b, it can be prevented that a difference in the ease of entering the loops is made due to, for example, the difference in the separation distance D1 depending on the engaging element. Therefore, the loops can be similarly inserted into any space between the first engaging pawl portion 13a and the second engaging pawl portion 13b. As a result, the non-woven fabric can be stably engaged with the molded surface fastener 1.

In addition, in the case of Embodiment 1, the first engaging elements 10a and the second engaging elements 10b having different thicknesses from each other are alternately arranged in each row in the cross direction CD. Therefore, the strengths and weaknesses of the engaging elements 10 between the first engaging element 10a and the second engaging element 10b, especially the strengths and weaknesses of the engaging element 10 with respect to the structure and shape of the loops of the non-woven fabric, can be easily complemented with each other.

Therefore, the molded surface fastener 1 of Embodiment 1 can be less likely to cause strengths and weaknesses with respect to various non-woven fabrics, thereby, desired performance such as peel strength with respect to more types of non-woven fabrics can be exerted appropriately and stably. As a result, it is possible to prevent the use of the molded surface fastener from being limited due to the compatibility with the non-woven fabric as in the conventional case, and to reduce the cost burden of the final products due to the selection of the non-woven fabric.

Conventionally, for example, in order to make the molded surface fastener manufactured long and wide into a size that can be attached to a product such as a diaper, the manufactured molded surface fastener 1 is first cut along the machine direction MD to produce narrow molded surface fasteners in some cases. In this case, in the molded surface fastener 1 of Embodiment 1, the first element rows 15a and the second element rows 15b are provided along the machine direction MD, and the positions of the first engaging elements 10a and the second engaging elements 10b are shifted along the machine direction MD. Further, as described above, between the first element row 15a and the second element row 15b adjacent to the first element row 15a in the cross direction CD, the widthwise space region S1 in the cross direction CD in which the stem portions 11 are not protruded on the base portion 5 and the engaging elements 10 are not provided in the CD direction in the plan view is continuously formed along the MD direction with an appropriate width dimension.

Therefore, when the molded surface fastener 1 of Embodiment 1 is cut along the machine direction MD, the molded surface fastener 1 is cut in the widthwise space regions S1, thereby, the engaging elements 10 do not (or are less likely to) interfere with cutting processing. Further in Embodiment 1, the molded surface fastener 1 is cut in the lengthwise space region S2, thereby, it is also possible to cut the molded surface fastener 1 along the cross direction CD without being hindered by the engaging elements 10. Therefore, the molded surface fastener 1 manufactured by the manufacturing apparatus 30 shown in FIG. 7, for example, can be easily cut to a size to be attached to the products.

The molded surface fastener 1 of Embodiment 1 described above is formed such that two types of the first engaging elements 10a and the second engaging elements 10b having different thicknesses from each other are arranged on the base portion 5 in the staggered pattern, and the first element rows 15a and the second element rows 15b are alternately provided in a width direction. However, it is also possible that the molded surface fastener of the present invention is formed such that three or more types of engaging elements having different thicknesses from each other are arranged on the base portion in the staggered pattern, and three or more types of element rows formed from engaging elements having different thicknesses are provided regularly in the width direction. In the present invention, for example, engaging strength can be controlled by changing the amount (type) of element rows having different thicknesses of the engaging elements depending on a desired loop member (non-woven fabric or the like).

Further, in the above-described Embodiment 1, the primary molded body 6 in which a plurality of provisional elements 20 stands on the base portion 5 as shown in FIG. 10 is molded by the molding apparatus 40, and then a part of the provisional element 20 is deformed by using the heat press apparatus 50 to manufacture the molded surface fastener 1 as shown in FIG. 1 and FIG. 2. In the present invention, however, it is also possible to provide the primary molded body 6 in which the plurality of provisional elements 20 stands on the base portion 5 shown in FIG. 10 as it is as a molded surface fastener.

Further, in the above-mentioned Embodiment 1, by changing the position of the pickup roller 43, the interval between the upper side holding roller 43a and the lower side holding roller 43b in the pickup roller 43, or the like, for example, when the primary molded body 6 is peeled off from the die wheel 41 of the molding apparatus 40, it is also possible that a pair of provisional pawl portions 23 of each provisional element 20 are deformed so as to slope downward toward the base portion 5 from side end edges of the rib portion 22 by holding the primary molded body 6 with the pickup roller 43. In the present invention, it is also possible to provide a primary molded body having the provisional elements in which the provisional pawl portions are sloped downward from the rib portion in this manner as it is as a molded surface fastener. Further, in the present invention, not only in the case of Embodiment 1 but also in a case of Embodiment 2, described later, it is also possible to provide a primary molded body molded in a primary molding step as it is as a molded surface fastener.

Embodiment 2

Figure 13:
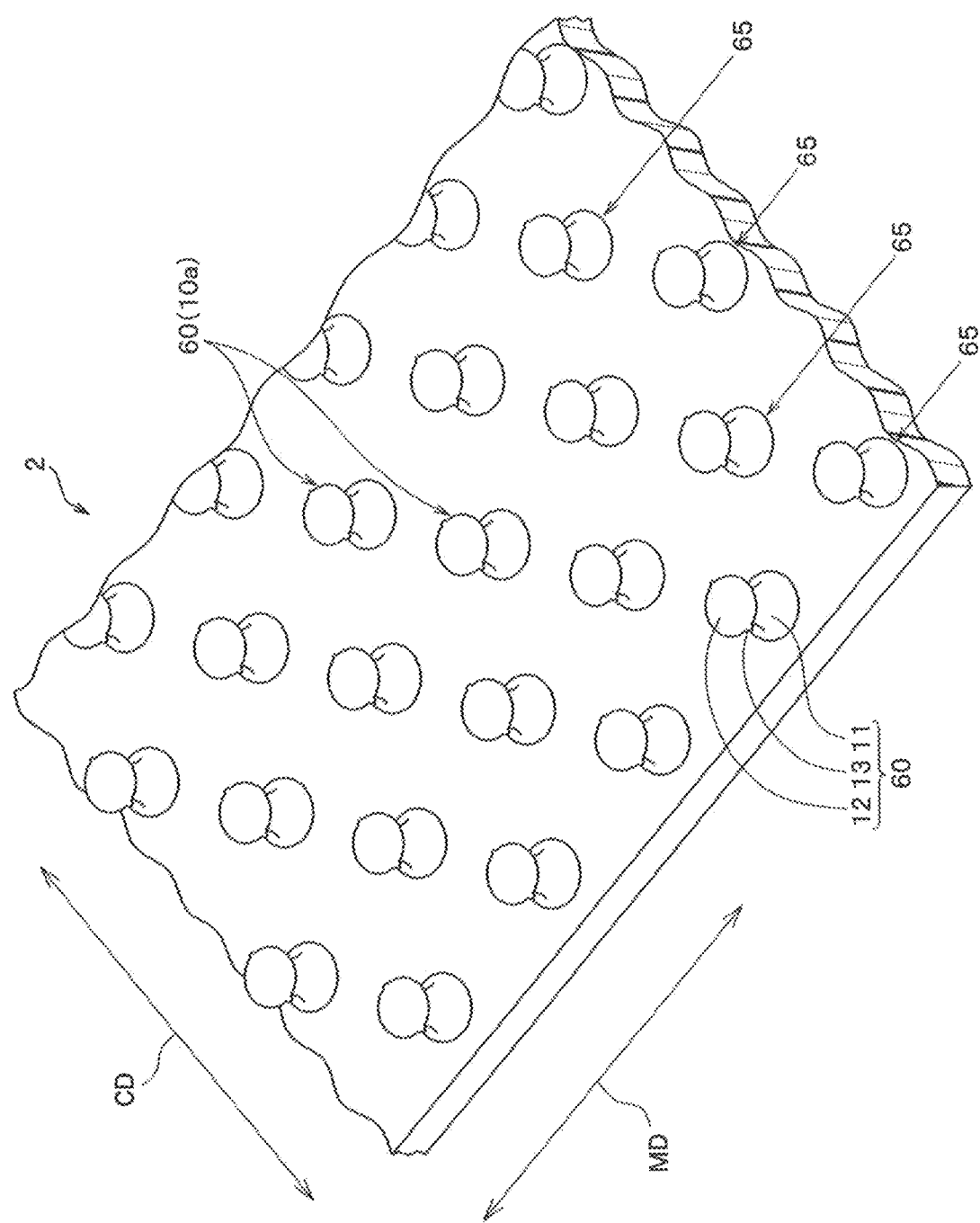
FIG. 13 is a perspective view illustrating a molded surface fastener according to Embodiment 2 of the present invention.
Figure 14:
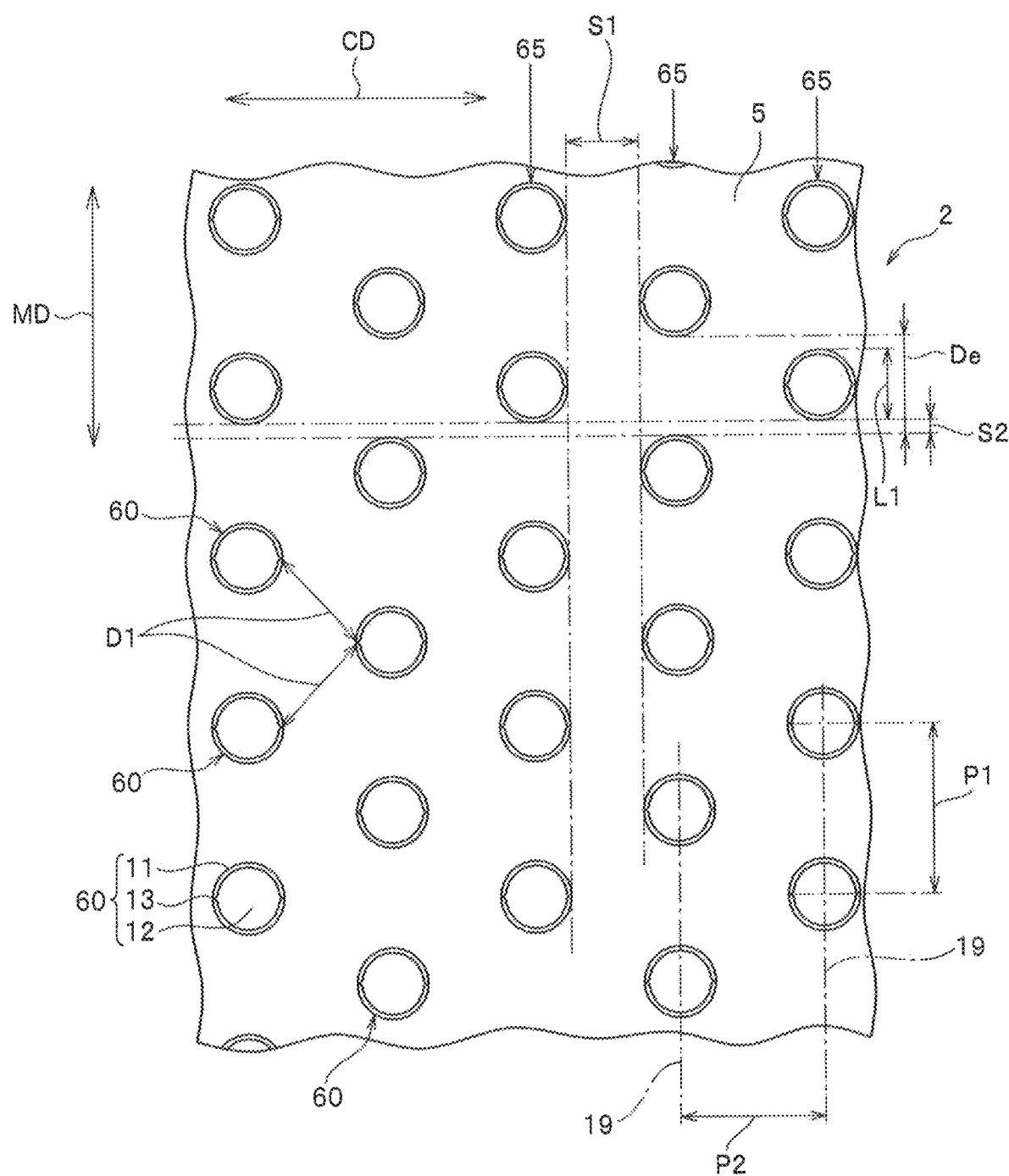
FIG. 14 is a plan view of the molded surface fastener.

FIG. 13 is a perspective view illustrating a molded surface fastener according to Embodiment 2, and FIG. 14 is a plan view of the molded surface fastener.

In Embodiment 2 and Embodiment 3 described later, the structure different from the molded surface fastener according to the above-mentioned Embodiment 1 will be mainly explained, and the portion or member having substantially the same structure as the molded surface fastener according to the above-mentioned Embodiment 1 will be represented with the same reference signs and will not be explained.

The molded surface fastener 2 of Embodiment 2 is formed by arranging only the above-mentioned first engaging elements 10a of Embodiment 1 as engaging elements 60 standing on an upper surface of a base portion 5. That is, in Embodiment 2, unlike the molded surface fastener 1 formed by using two types of the engaging elements 10, which are the first engaging elements 10a and the second engaging elements 10b in the above-mentioned Embodiment 1, the molded surface fastener 2 is formed by using only one type of engaging element 60, which is the first engaging element 10a. The molded surface fastener 2 of Embodiment 2 is formed in the same manner as the above-mentioned molded surface fastener 1 of Embodiment 1, except for using only the first engaging elements 10a as engaging elements.

Specifically, the molded surface fastener 2 of Embodiment 2 has a flat plate-shaped base portion 5 and a plurality of engaging elements 60 (first engaging elements 10a) standing on the upper surface of the base portion 5.

Further, each engaging element 60 has a substantially truncated cone-shaped stem portion 11, an engaging head portion 12 formed integrally on the stem portion 11 via a boundary portion 14, and two micro engaging pawl portions 13 protruded on an outer peripheral edge part of the engaging head portion 12. The two engaging pawl portions 13 of each engaging element 60 are, in a plan view of the engaging element 60, when an imaginary center line is drawn along a machine direction MD at a middle position in a cross direction CD of the stem portion 11 and the engaging head portion 12, protruded in opposite directions to each other in the cross direction CD at positions that are line-symmetrical with each other with respect to the imaginary center line.

In the molded surface fastener 2 of Embodiment 2, the plurality of engaging elements 60 is arranged in a line along the machine MD at a predetermined pitch interval P1 to form an element row 65. Further, a plurality of the element rows 65 is placed side by side in the cross direction CD at a predetermined pitch interval P2.

Further, between the two element rows 65 adjacent to the cross direction CD, the engaging elements 60 forming one element row 65 and the engaging elements 60 forming the other element row 65 are, regarding the positions of the machine direction MD, disposed at positions shifted from each other by half the size of the pitch interval P1 in the machine direction MD between the engaging elements 60 in each element row 65. Therefore, the engaging elements 60 forming the plurality of element rows 65 are arranged on the base portion 5 in a staggered pattern.

Therefore, as shown in FIG. 14, in the two element rows 65 adjacent to each other in the cross direction CD, a separation distance D1 between the engaging pawl portion 13 (engaging pawl portion 13 facing one element row 65) provided on one side in the cross direction CD of the engaging element 60 in the other element row 65 and the engaging pawl portion 13 (engaging pawl portion 13 facing the other element row 65) provided on the other side in the cross direction CD of the engaging element 60 in one element row 65 can be made the same size for all the engaging elements 60.

Further, between the two element rows 65 adjacent to each other in the cross direction CD, as shown in FIG. 14, there are provided widthwise space regions S1 in the cross direction CD in which the engaging elements 60 are not provided. Each widthwise space region S1 in the cross direction CD is formed linearly and continuously along the machine direction MD as a region in which the stem portions 11 are not protruded on the base portion 5 and the engaging elements 60 are not overlapped. Furthermore, in the case of Embodiment 2, the pitch interval P2 in the cross direction CD between the element rows 65 is set to be larger than half the size of the pitch interval P1 in the machine direction MD between the engaging elements 60 in each element row 65, as in the case of the above-mentioned Embodiment 1.

Further in Embodiment 2, a minimum element separation distance (minimum value of the distance between the engaging elements 60 adjacent to each other in the machine direction MD) De in each element row 65 is set to be larger than a maximum dimension L1 in the machine direction MD of each engaging element 60 in the element row 65. Thereby, each lengthwise space region S2 in the machine direction MD in which the engaging elements 60 are not provided is provided linearly and continuously over the entire the molded surface fastener 2 in the cross direction CD. Therefore, in the molded surface fastener 2, it is possible to prevent the above-mentioned separation distance D1 between the engaging pawl portions 13 from becoming too long, and to stably secure appropriate peel strength and shear strength.

The molded surface fastener 2 of Embodiment 2 as described above is manufactured by using the manufacturing apparatus 30 shown in FIG. 7 in substantially the same manner as in the case of Embodiment 1.

In the case of Embodiment 2, although not shown, penetration holes provided on an outer side cylindrical body 44 in a cylindrical shape disposed on the die wheel 41 are not formed in two sizes of the above-mentioned first penetration hole 47a and the second penetration hole 47b, and all the penetration holes are formed in the same size. The molded surface fastener 2 of Embodiment 2 is manufactured in the same manner as in the case of Embodiment 1, except that the size of the penetration holes provided on the outer side cylindrical body 44 is different.

In the above-mentioned molded surface fastener 2 of Embodiment 2, a right and left pair of engaging pawl portions 13 are provided on the engaging head portion 12 of each engaging element 60, and the pair of engaging pawl portions 13 are protruded from symmetrical positions of the engaging head portion 12 along the cross direction CD. Thereby, the molded surface fastener 2 of Embodiment 2 can easily obtain high peel strength with respect to a non-woven fabric as in the molded surface fastener 1 of Embodiment 1.

Further, since the plurality of engaging elements 60 is regularly arranged on the base portion 5 in the staggered pattern as described above, for all the engaging elements 60 between the two element rows 65 adjacent to each other in the cross direction CD, the separation distance D1 between the engaging pawl portion 13 of the engaging element 60 in one element row 65 and the engaging pawl portion 13 of the engaging element 60 in the other element row 65 can be made the same size.

Therefore, in the molded surface fastener 2 of Embodiment 2, it is possible to insert loops between any engaging pawl portions 13 between the two element rows 65 adjacent to each other in the same manner, and to stably engage a plurality of the loops with the engaging elements 60. Thus, the molded surface fastener 2 of Embodiment 2 can be less likely to cause strengths and weaknesses with respect to various non-woven fabrics, and thus exert desired performance such as peel strength with respect to more types of non-woven fabrics appropriately and stably.

Embodiment 3

Figure 15:
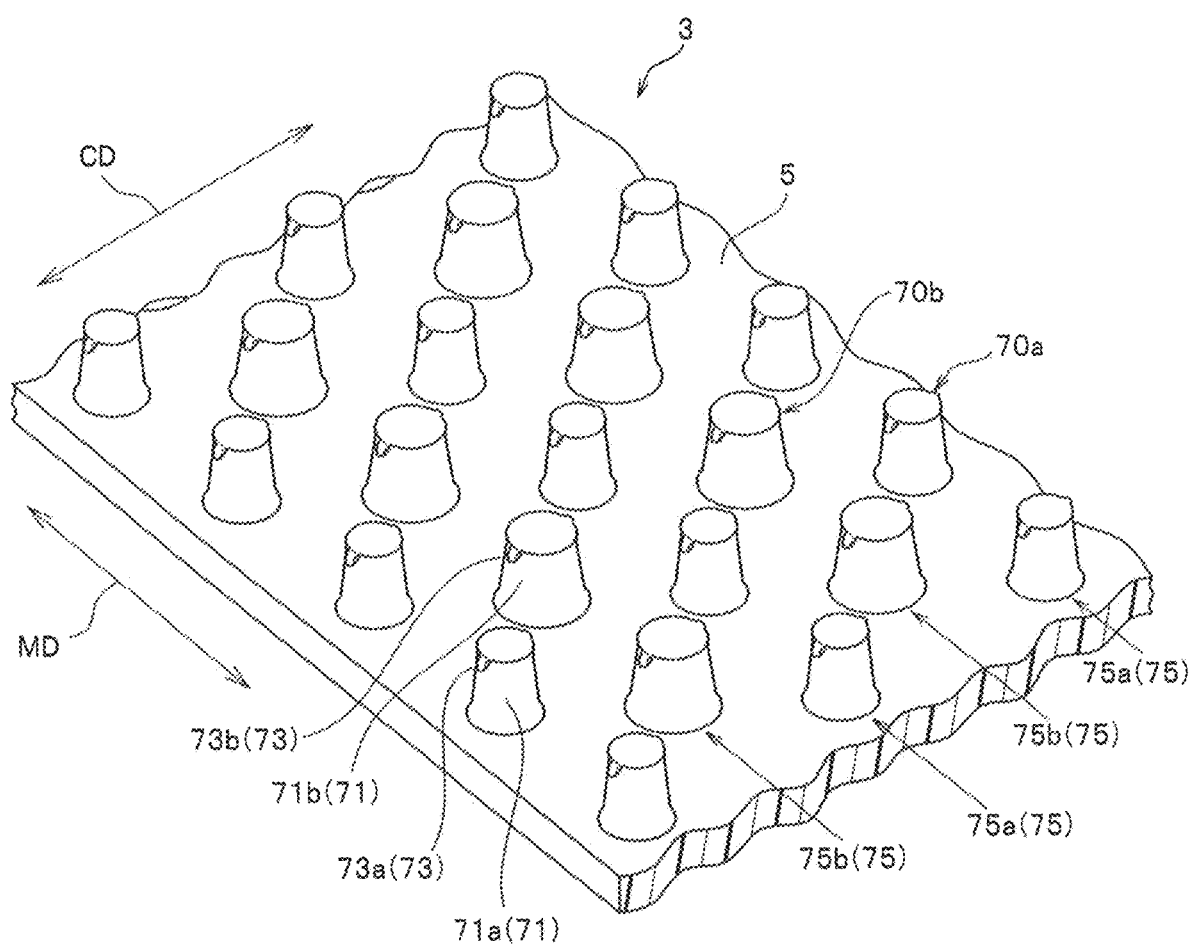
FIG. 15 is a perspective view illustrating a molded surface fastener according to Embodiment 3 of the present invention.
Figure 16:
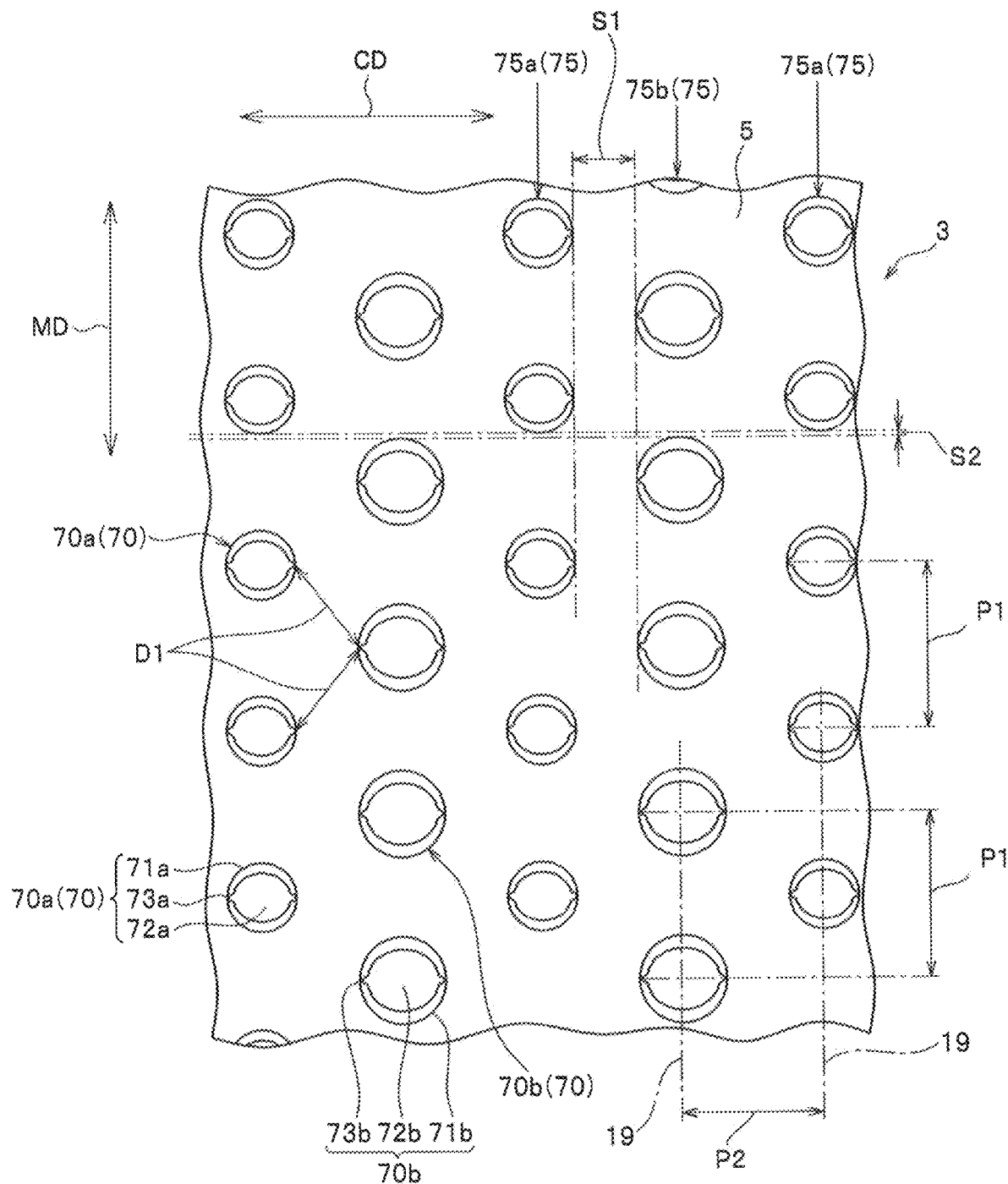
FIG. 16 is a plan view of the molded surface fastener.
Figure 17:
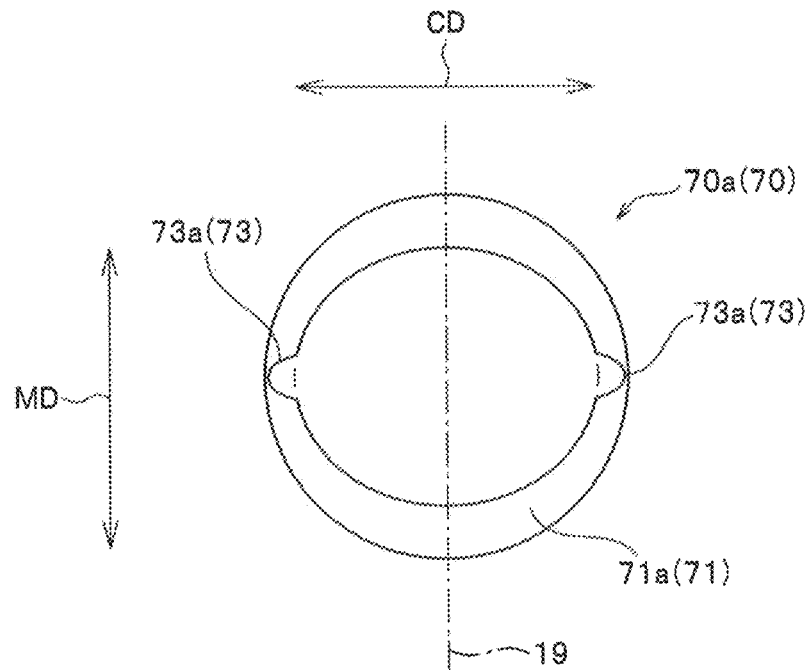
FIG. 17 is a plan view illustrating a first engaging element of the molded surface fastener.
Figure 18:
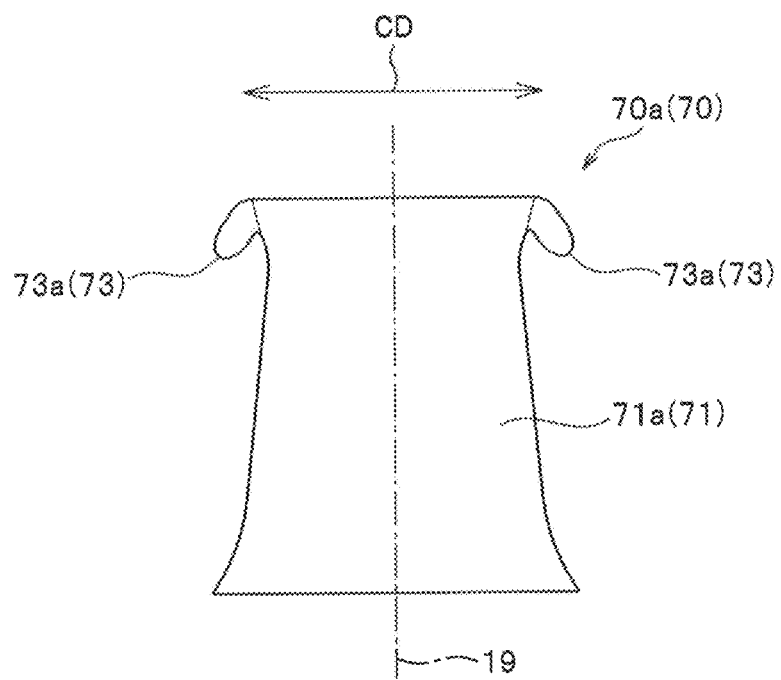
FIG. 18 is a front view of the first engaging element when viewed from the machine direction.
Figure 19:
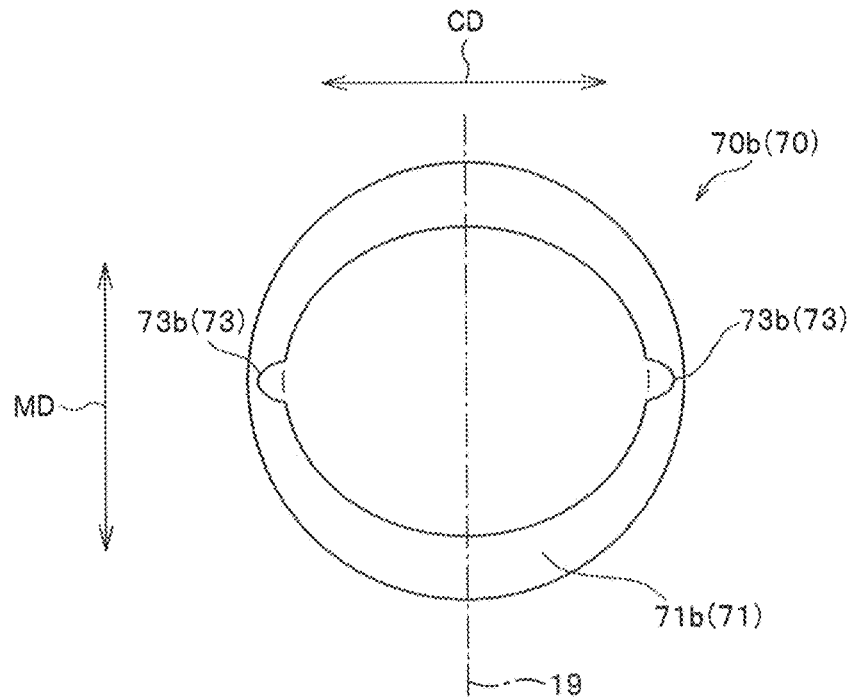
FIG. 19 is a plan view illustrating a second engaging element of the molded surface fastener.
Figure 20:
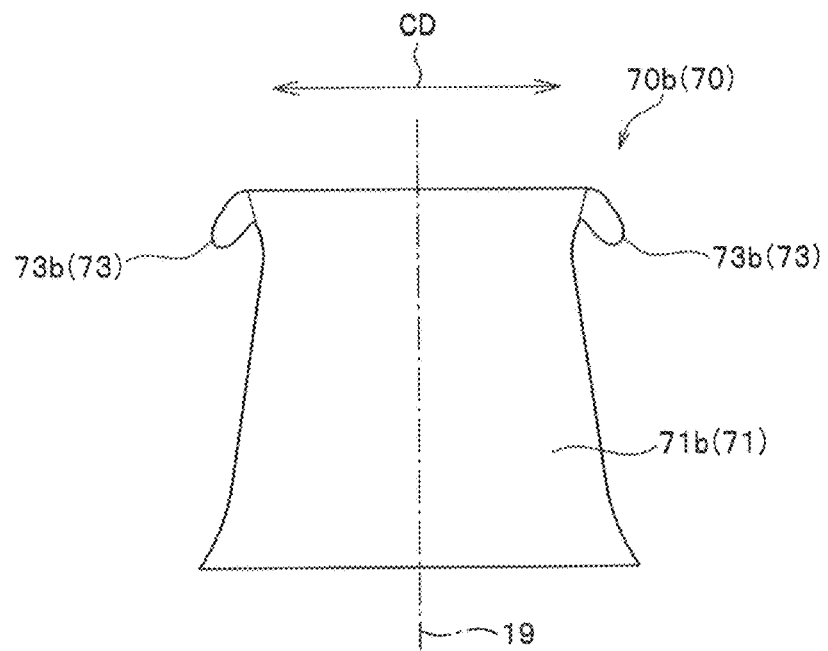
FIG. 20 is a front view of the second engaging element when viewed from the machine direction.
Figure 21:
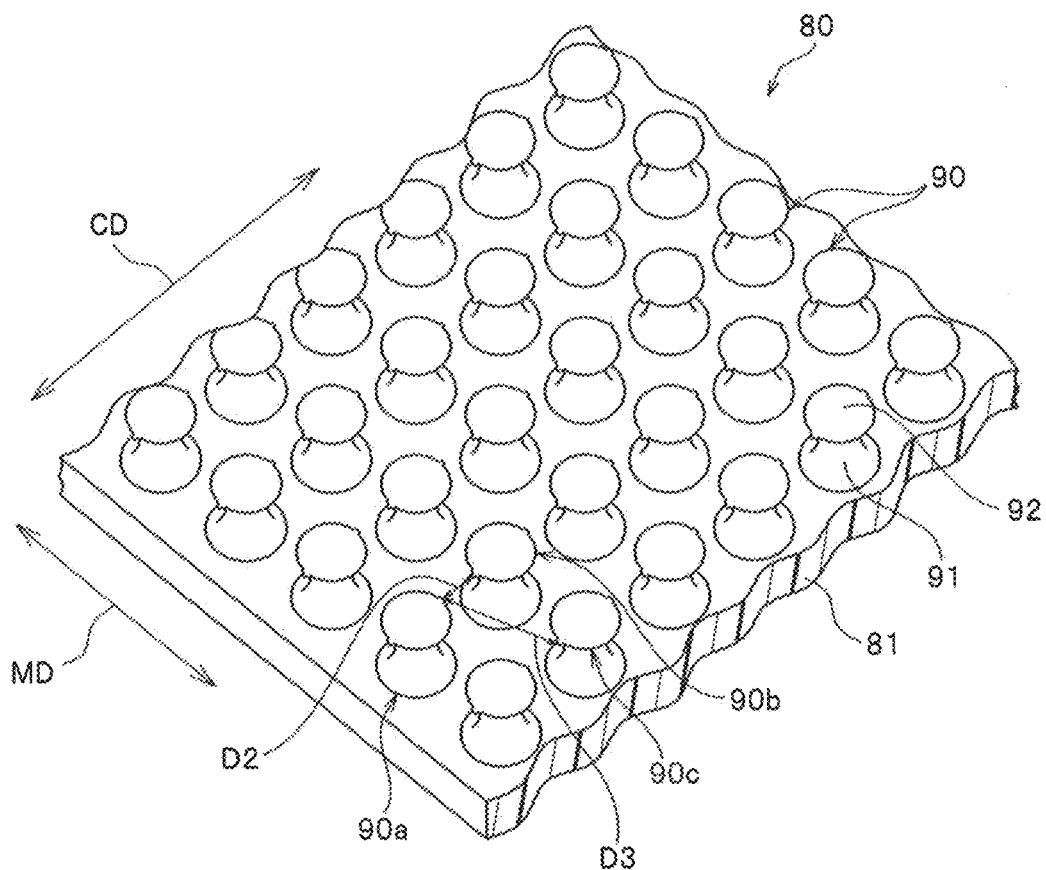
FIG. 21 is a perspective view illustrating a conventional molded surface fastener.
Figure 22:
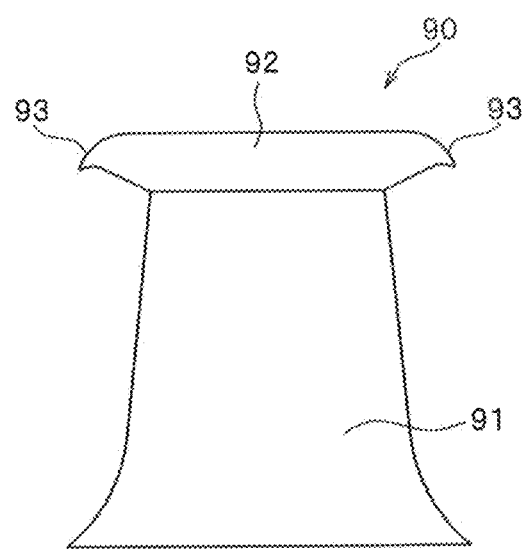
FIG. 22 is a plan view illustrating an engaging element of the conventional molded surface fastener when viewed from the machine direction.

FIG. 15 is a perspective view illustrating a molded surface fastener according to Embodiment 3, and FIG. 16 is a plan view of the molded surface fastener. FIG. 17 and FIG. 18 are an enlarged plan view and a front view illustrating a first engaging element of the molded surface fastener. FIG. 19 and FIG. 20 are an enlarged plan view and a front view illustrating a second engaging element of the molded surface fastener.

The molded surface fastener 3 of Embodiment 3 has a flat plate-shaped base portion 5 and a plurality of engaging elements 70 standing on an upper surface of the base portion 5. The engaging elements 70 have first engaging elements 70a and second engaging elements 70b which is thicker than the first engaging element 70a. Each engaging element 70 has a stem portion 71 standing on the base portion 5 and two micro engaging pawl portions 73 protruded on an outer peripheral side surface of the stem portion 71. In this case, the stem portion 71 and the engaging pawl portions 73 of the first engaging element 70a are referred to as a first stem portion 71a and a first engaging pawl portion 73a, and similarly in the second engaging element 70b, referred to as a second stem portion 71b and a second engaging pawl portion 73b.

The stem portion 71 (the first stem portion 71a and the second stem portion 71b) of Embodiment 3 has a partially deformed shape similar to a truncated cone such that a cross-sectional area perpendicular to an upper and lower direction decreases gradually as separating from the base portion 5 except for an upper end part of the stem portion 71, and the cross-sectional area increases slightly toward upward in the upper end part of the stem portion 71.

The upper end part of the stem portion 71 is formed such that the cross-sectional area perpendicular to the upper and lower direction increases slightly toward upward by pressing a provisional element 20 from above in a secondary molding step when manufacturing the molded surface fastener 3. An upper end surface of the stem portion 71 is formed to be a flat surface parallel to the upper surface of the base portion 5, and has a slightly long oval shape in a cross direction CD in a plan view of the engaging element 70. It is also possible that the stem portion 71 of Embodiment 3 is formed to be a truncated cone shape same as the stem portion 71 of Embodiment 1 as mentioned above, a truncated pyramid shape such as a truncated square shape, a columnar shape, or a prismatic shape such as a square prism shape.

In Embodiment 3, the oval-shaped upper end surface of the first engaging element 70a and the oval-shaped upper end surface of the second engaging element 70b have a similar relationship with each other. In this case, the area of the oval-shaped upper end surface of the second engaging element 70b is 125% or larger and 250% or smaller, preferably 150% or larger and 200% or smaller of the area of the oval-shaped upper end surface of the first engaging element 70a.

Further, a height dimension of the first engaging element 70a from the upper surface of the base portion 5 to the upper end surface of the first stem portion 71a and a height dimension of the second engaging element 70b from the upper surface of the base portion 5 to the upper end surface of the second stem portion 71b are set to be the same size. Therefore, the feel of the top surface of the molded surface fastener 3 can be improved.

A pair of engaging pawl portions 73 provided in each engaging element 70 are protruded outward from the outer peripheral side surface of the upper end part of the stem portion 71. The two engaging pawl portions 73 are, in the plan view of the engaging element 70, when an imaginary center line 19 is drawn along a machine direction MD at a middle position in the cross direction CD on the upper end surface of the stem portion 71, provided as a pair of symmetrical engaging pawl portions 73 at positions that are line-symmetrical with each other with respect to the imaginary center line 19.

In this case, the pair of engaging pawl portions 73 of each engaging element 70 are, in the plan view of the engaging element 70, protruded in opposite directions to each other in the cross direction CD (right and left direction) from the outer peripheral side surface of the stem portion 71 at a middle part in the machine direction MD. Further, the right and left engaging pawl portions 73 have a shape in which each engaging pawl portion is sloped downward from the outer peripheral side surface of the stem portion 71 toward the base portion 5 so that the protruded tip end hangs downward. Therefore, a gap is formed between the engaging pawl portion 73 and the outer peripheral side surface of the stem portion 71.

In Embodiment 3 as well, as in the case of Embodiment 1, at least a set of two symmetrical engaging pawl portions 73 may be provided in the engaging element 70 at the line-symmetrical positions with each other with respect to the above-mentioned imaginary center line 19, and therefore, two symmetrical engaging pawl portions can be provided at symmetrical positions in one end part or the other end part in the machine direction MD of the engaging head portion 12, for example. Further, it is also possible to provide the pair of symmetrical engaging pawl portions 73 and other engaging pawl portions, or to provide two sets of two symmetrical engaging pawl portions 73 for one engaging element 70.

Further, in Embodiment 3, the first engaging pawl portion 73a of the first engaging element 70a and the second engaging pawl portion 73b of the second engaging element 70b are formed to have substantially the same size. A width dimension of the engaging pawl portion 73 at the base end part is the same for both the first engaging element 70a and the second engaging element 70b.

In the molded surface fastener 3 of Embodiment 3, a plurality of element rows 75 is formed by arranging the plurality of engaging elements 70 along the machine direction MD at a predetermined pitch interval P1. In this case, as a plurality of element rows 75, first element rows 75a formed by a plurality of first engaging elements 70a and second element rows 75b formed by a plurality of second engaging elements 70b are placed alternately side by side in the cross direction CD at a predetermined pitch interval P2.

Further in this case, the first engaging elements 70a forming the first element row 75a and the second engaging elements 70b forming the second element row 75b are, regarding the positions in the machine direction MD, arranged to be shifted from each other by half the size of the pitch interval P1 in the machine direction MD between the engaging elements 70 in the element row 75. Thereby, the plurality of first engaging elements 70a and the plurality of second engaging elements 70b are regularly arranged on the base portion 5 in a staggered pattern having an alternating positional relationship in the machine direction MD at a predetermined interval.

Therefore, as in the case of Embodiment 1, in the first element row 75a and the second element row 75b adjacent to each other in the cross direction CD of the molded surface fastener 3 of Embodiment 3, a separation distance D1 between the first engaging pawl portion 73a provided on one side of the cross direction CD in the first engaging element 70a and the second engaging pawl portion 73b provided on the other side of the cross direction CD in the second engaging element 70b can be made the same size for all the engaging elements 70.

Further, also in the molded surface fastener 3 of Embodiment 3, as in the case of above-mentioned Embodiment 1, widthwise space regions S1 in the cross direction CD in which the first engaging elements 70a and the second engaging elements 70b are not provided are linearly and continuously provided along the machine direction MD between the first element row 75a and the second element row 75b adjacent to each other in the cross direction CD.

Further, since each minimum element separation distance in the second element row 75b and the first element row 75a is set to be larger than maximum dimensions in the machine direction MD of the first engaging element 70a and the second engaging element 70b, lengthwise space regions S2 in the machine direction MD in which the first engaging elements 70a and the second engaging element 70b are not provided are provided linearly and continuously over the entire molded surface fastener 3 in the cross direction CD.

The molded surface fastener 3 of Embodiment 3 as mentioned above is manufactured in substantially the same manner as in the case of the above-mentioned Embodiment 1 by using a manufacturing apparatus 30 shown in FIGS. 7 to 9. In this case, an upper side press roller 51 and a lower side press roller 52 of a heat press apparatus 50 are adjusted by a height adjusting means (not shown) such that a distance between both rollers 51 and 52 is slightly larger than in the case of the above-mentioned Embodiment 1.

In the case of manufacturing the molded surface fastener 3 of Embodiment 3, firstly, a primary molding step for molding a primary molded body 6 is conducted by a molding apparatus 40. The primary molding step of Embodiment 3 is conducted in the same manner as the primary molding step of the above-mentioned Embodiment 1, thereby, the primary molded body 6 in which the plurality of provisional elements 20 is standing on the base portions shown in FIG. 10 is molded as in the case of Embodiment 1 described above.

Subsequently, the primary molded body 6 which has been peeled off from the die wheel 41 by the pickup roller, is introduced between the upper side press roller 51 and the lower side press roller 52 of the heat press apparatus 50 that performs a secondary molding step. Thereby, an upper end part of a provisional stem portion 21, a rib portion 22, and a pair of provisional pawl portions 23 in each provisional element 20 are heated and softened by the upper side press roller 51, and the rib portion 22 and a part of the pair of provisional pawl portions 23 are pressed by the upper side press roller 51.

In the secondary molding step with the heat press apparatus 50, the upper end part of the provisional stem portion 21, the rib portion 22, and a part of the pair of provisional pawl portions 23 in each provisional element 20 are thermally deformed so as to be flattened while spreading radially as a whole, thus, the engaging element 70 of Embodiment 3 is molded from each provisional element 20. As a result, the molded surface fastener 3 of Embodiment 3 is manufactured as shown in FIGS. 15 and 16.

The molded surface fastener 3 of Embodiment 3 manufactured as above can obtain substantially the same effect as the molded surface fastener 1 of the above-mentioned Embodiment 1. That is, the molded surface fastener 3 of Embodiment 3 can stably engage a non-woven fabric, and can easily obtain high peel strength with respect to the non-woven fabric. Further, the molded surface fastener 3 of the Embodiment 3 can mutually complement easily the strengths and weaknesses of the engaging element 70 with respect to the structure and shape of the loops of the non-woven fabric between the first engaging element 70a and the second engaging element 70b. Therefore, it is possible to less likely to occur strengths and weaknesses for various non-woven fabrics.

In the molding apparatus 40 used for manufacturing the molded surface fastener 1, 2, 3 of the above-mentioned Embodiments 1 to 3, by corresponding the forming interval in the machine direction MD of the first penetration holes 47a and the second penetration holes 47b provided on the outer side cylindrical body 44 of the molding apparatus 40 and the interval in the machine direction MD of the grooved channel portions 48 formed on the inner side cylindrical body 45 to each other, the position of each grooved channel portion 48 on the inner side cylindrical body 45 is overlapped with the diameters of the first penetration hole 47a and the second penetration hole 47b formed on the outer side cylindrical body 44, as shown in FIG. 9. That is, in the outer side cylindrical body 44 and the inner side cylindrical body 45 of the molding apparatus 40 used in the above-mentioned Embodiments 1 to 3, one grooved channel portion 48 on the inner side cylindrical 45 is provided to be inevitably overlapped with one first penetration hole 47a provided on the outer side cylindrical body 44.

In the present invention, however, the forming interval in the machine direction MD of the first penetration holes and the second penetration holes provided on the outer side cylindrical body and the interval in the machine direction MD of the grooved channel portions formed on the inner side cylindrical body can be shifted intentionally with a predetermined size. Specifically, the grooved channel portion on the inner side cylindrical body can be intentionally smaller than half the size of the forming interval in the machine direction MD of the first penetration holes on the outer side cylindrical body. In this case, the number of the grooved channel portions in the machine direction MD formed on the inner side cylindrical body can be larger than the total number of the first penetration holes and the second penetration holes provided on the outer side cylindrical body in the machine direction MD.

Thereby, it is possible that only one type of engaging element 10, 60, 70 having a predetermined shape is not disposed, for example, as in the case of the molded surface fastener 1, 2, 3 of Embodiments 1 to 3 as above, but two or more types of engaging elements having different shapes from each other are formed to be appeared respectively in a predetermined cycle.

In this case, particularly, in one element row, it is possible to form two or more types of engaging elements 10, 17, 18 as shown in the plan view of FIGS. 3, 11, and 12, for example, that is, two or more types of engaging elements having different positions or numbers of the pair of symmetrical engaging pawl portions that are symmetrical in a width direction.

Further, when two or more types of engaging elements are formed in one element row in this manner, one type of engaging element having the same shape is formed in the element row in every predetermined cycle. For example, in a case that nine types of engaging elements are formed in one element row, in the element row, engaging elements having the same shape are periodically formed for every nine engaging elements along the machine direction MD.

In addition to the structures of the molded surface fasteners 1, 2 and 3 of Embodiments 1 to 3 described above, by further forming two or more types of engaging elements having different shapes intentionally and periodically in one element row along the machine direction MD to manufacture a molded surface fastener, between different types of the engaging elements having different shapes in the manufactured molded surface fastener, the strengths and weaknesses of each engaging element can be complemented to each other with respect to a non-woven fabric. Therefore, such a molded surface fastener can more stably and appropriately exert desired performance such as peel strength with respect to various non-woven fabrics.

REFERENCE SIGNS LIST 1,2,3 Molded surface fastener
5 Base portion
6 Primary molded body
10 Engaging element
10a First engaging element
10b Second engaging element
11 Stem portion
11a First stem portion
11b Second stem portion
12 Engaging head portion
12a First engaging head portion
12b Second engaging head portion
13 Engaging pawl portion (Symmetrical engaging pawl portion)
13a First engaging pawl portion
13b Second engaging pawl portion
14 Boundary portion
15 Element row (MD element row)
15a First element row
15b Second element row
17 Engaging element
18 Engaging element
19 Center line
20 Provisional element
20a First provisional element
20b Second provisional element
21 Provisional stem portion
21a First provisional stem portion
21b Second provisional stem portion
22 Rib portion
22a Frist rib portion
22b Second rib portion
23 Provisional pawl portion (Provisional engaging pawl portion)
23a First provisional pawl portion
23b Second provisional pawl portion
30 Manufacturing apparatus
40 Molding apparatus
41 Die wheel
42 Extrusion nozzle
43 Pickup roller
43a Upper side holding roller
43b Lower side holding roller
44 Outer side cylindrical body (Outer side sleeve)
45 Inner side cylindrical body (Inner side sleeve)
46 Rotation driving roller
47 Penetration hole
47a First penetration hole
47b Second penetration hole
48 Grooved channel portion
50 Heat press apparatus
51 Upper side press roller (Upper side calender roller)
52 Lower side press roller (Lower side calender roller)
60 Engaging element
65 Element row
70 Engaging element 70a First engaging element
70b Second engaging element
71 Stem portion
71a First stem portion
71b Second stem portion
73 Engaging pawl portion (Symmetrical engaging pawl portion)
73a First engaging pawl portion
73b Second engaging pawl portion
75 Element row (MD element row)
75a First element row
75b Second element row
D1 Separation distance
De Minimum element separation distance
L1 Maximum value of dimension in machine direction of engaging element
P1 Pitch interval of engaging element in element row
P1a Pitch interval of engaging element in first element row
P1b Pitch interval of engaging element in second element row
P2 Pitch interval of element row
S1 Widthwise space region
S2 Lengthwise space region

The invention claimed is:

1. A molded surface fastener made of synthetic resin comprising a flat plate-shaped base portion formed to be long in a machine direction and a plurality of engaging elements standing on an upper surface of the base portion, in which the engaging element comprises a stem portion standing on the upper surface of the base portion and at least two engaging pawl portions protruding outward at a top end part of the engaging element, wherein the plurality of the engaging elements is disposed in a line at a predetermined pitch interval along the machine direction of the base portion to form an element row,
a plurality of the element rows is arranged side by side in a cross direction perpendicular to the machine direction,
each of the engaging elements has, as the engaging pawl portions, at least a pair of symmetrical engaging pawl portions which are disposed at symmetrical positions with each other with respect to an imaginary center line located in a middle of the cross direction of the stem portion in a plan view of the engaging element, and are protruded respectively in the cross direction sides,
a width dimension between a pair of side wall surfaces of each of the symmetrical engaging pawl portions is ⅓ or smaller of the dimension in the machine direction of an upper end part of the stem portion in the engaging element, and
the engaging elements in each element row are disposed at a position shifted by half a size of the pitch interval in the machine direction with respect to a position of the engaging elements in the element rows adjacent to each other in the cross direction.

2. The molded surface fastener according to claim 1, wherein
a plurality of the element rows is disposed at a predetermined pitch interval in the cross direction,
widthwise space regions in which the engaging elements are not provided are disposed along the machine direction between the element rows adjacent to each other in the cross direction, and
the pitch interval of the element rows in the cross direction is larger than half the size of the pitch interval in the machine direction.

3. The molded surface fastener according to claim 1, wherein
in a plan view of the molded surface fastener, a minimum element separation distance between the engaging elements adjacent to each other in the machine direction in each element row is larger than a maximum value of a dimension in the machine direction of the engaging element in other element rows adjacent to the element row in the cross direction, and
lengthwise space regions in which the engaging elements are not provided are disposed along the cross direction over the entire molded surface fastener in the cross direction.

4. The molded surface fastener according to claim 1, wherein
widthwise space regions in which the engaging elements are not provided are disposed along the machine direction between the element rows adjacent to each other in the cross direction, and
a dimension of a lengthwise space region in the machine direction is smaller than a dimension of the widthwise space region in the cross direction.

5. The molded surface fastener according to claim 1, wherein in a plan view of the molded surface fastener, a minimum element separation distance between the engaging elements adjacent to each other in the machine direction in each element row is equal to or smaller than a maximum value of a dimension in the machine direction of the engaging element in other element rows adjacent to the element row in the cross direction.

6. The molded surface fastener according to claim 1, wherein
the engaging elements are formed such that an upper end surface or an upper end cross-section at an upper end part of each stem portion perpendicular to a standing direction of the stem portion has the same shape and same area as each other for each element row, and
at least two types of the element rows in which the areas of the upper end surfaces or the upper end cross-sections of the stem portions are different from each other are provided.

7. The molded surface fastener according to claim 1, wherein
the element rows include first element rows in which an area of an upper end surface or an upper end cross-section at an upper end part in each of the stem portions perpendicular to a standing direction of the stem portion is a first size and second element rows in which an area of the upper end surface or the upper end cross-section in each of the stem portions is a second size to be larger than the first size are provided, and
the first element rows and the second element rows are alternately arranged in the cross direction.

8. The molded surface fastener according to claim 7, wherein
the upper end surface or the upper end cross-section in each of the stem portions in the first element rows and the upper end surface or the upper end cross-section in each of the stem portions in the second element rows have a shape similar to each other, and
a height dimension of each engaging element in the first element rows from the base portion and a height dimension of each engaging element in the second element rows from the base portion are the same.

9. The molded surface fastener according to claim 1, wherein a pair of the symmetrical engaging pawl portions are, in a plan view of the engaging element, disposed in a middle part of the stem portion in the machine direction and protruded each other in opposite directions along the cross direction, and with respect to the engaging elements in each element row, each of the other element rows adjacent to the element row in the cross direction includes two engaging elements in which respective separation distances between the symmetrical engaging pawl portion of the element row and the symmetrical engaging pawl portion of the other element row are equal.

10. The molded surface fastener according to claim 1, wherein the engaging pawl portions are formed to be sloped or curved downward toward the base portion.

* * * * *